United States Patent
Sperl et al.

(10) Patent No.: US 11,823,401 B2
(45) Date of Patent: Nov. 21, 2023

(54) PATIENT FOLLOW-UP ANALYSIS

(71) Applicant: Siemens Healthcare GmbH, Erlangen (DE)

(72) Inventors: Jonathan Sperl, Bamberg (DE); Sven Bauer, Herzogenaurach (DE); Lutz Guendel, Erlangen (DE); Rainer Kaergel, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 550 days.

(21) Appl. No.: 16/951,182

(22) Filed: Nov. 18, 2020

(65) Prior Publication Data
US 2021/0166406 A1 Jun. 3, 2021

(30) Foreign Application Priority Data
Nov. 28, 2019 (EP) .................................. 19212054

(51) Int. Cl.
*G06T 7/38* (2017.01)
*G06T 7/33* (2017.01)
(Continued)

(52) U.S. Cl.
CPC ............ *G06T 7/38* (2017.01); *G06F 21/6245* (2013.01); *G06T 7/0016* (2013.01); *G06T 7/337* (2017.01);
(Continued)

(58) Field of Classification Search
CPC ......... G06T 7/38; G06T 7/0016; G06T 7/337; G06T 2207/10072; G06T 2207/30048;
(Continued)

(56) References Cited

U.S. PATENT DOCUMENTS

| 8,744,141 B2* | 6/2014 | Derakhshani | G06T 7/0014 |
| | | | 382/128 |
| 8,784,314 B2* | 7/2014 | Mathew | A61B 6/00 |
| | | | 600/437 |

(Continued)

FOREIGN PATENT DOCUMENTS

| CN | 1840709 A | * 10/2006 |
| DE | 102007026520 A1 | * 12/2008 |

(Continued)

OTHER PUBLICATIONS

Ghesu, Florian et al. "Multi-Scale Deep Reinforcement Learning for Real-Time 3D-Landmark Detection in CT Scans", IEEE, 2017, vol. 41, Nr. 1, pp. 1-14; 2017.

(Continued)

*Primary Examiner* — Mahendra R Patel
(74) *Attorney, Agent, or Firm* — Harness, Dickey & Pierce, P.L.C.

(57) ABSTRACT

A computer-implemented method for comparing follow-up medical findings includes receiving image data showing a body part of a patient at a first time and retrieving, from a database, reference data associated to the image data. The reference data includes reference biometric data and one or more reference medical findings. Thereby the reference biometric data and the one or more reference medical findings have been extracted from reference image data depicting the body part of the patient at a second time, different than the first time. The method further includes processing the received image data to extract, from the image data, biometric data corresponding to the reference biometric data and one or more medical findings; performing a registration of the extracted biometric data with the reference biometric data; and comparing the extracted medi- (Continued)

cal findings with the reference medical findings using the registration.

22 Claims, 4 Drawing Sheets

(51) Int. Cl.
    *G16H 10/60*     (2018.01)
    *G16H 30/20*     (2018.01)
    *G16H 30/40*     (2018.01)
    *G06F 21/62*     (2013.01)
    *G06T 7/00*     (2017.01)

(52) U.S. Cl.
    CPC ............. *G16H 10/60* (2018.01); *G16H 30/20* (2018.01); *G16H 30/40* (2018.01); *G06T 2207/10072* (2013.01)

(58) Field of Classification Search
    CPC ....... G06T 2207/30061; G06F 21/6245; G06F 16/583; G16H 10/60; G16H 30/20; G16H 30/40; G16H 50/20
    USPC ........................................................ 382/131
    See application file for complete search history.

(56) References Cited

U.S. PATENT DOCUMENTS

| | | | | |
|---|---|---|---|---|
| 10,977,390 | B2 * | 4/2021 | Blumhofer | G06T 5/002 |
| 2008/0310698 | A1 * | 12/2008 | Boeing | A61B 6/545 |
| | | | | 382/131 |
| 2009/0030731 | A1 * | 1/2009 | Reiner | G06Q 10/00 |
| | | | | 434/323 |
| 2011/0007954 | A1 * | 1/2011 | Suehling | G06V 40/10 |
| | | | | 382/128 |
| 2011/0081066 | A1 * | 4/2011 | Jolly | G06T 7/174 |
| | | | | 382/131 |
| 2012/0235679 | A1 * | 9/2012 | Xue | G01R 33/56509 |
| | | | | 324/307 |
| 2014/0313222 | A1 * | 10/2014 | Anderson | G06T 7/30 |
| | | | | 382/128 |
| 2015/0317789 | A1 * | 11/2015 | Codella | G06T 7/168 |
| | | | | 382/133 |
| 2017/0360578 | A1 * | 12/2017 | Shin | G09B 23/286 |
| 2018/0005083 | A1 * | 1/2018 | Georgescu | G06T 7/0012 |
| 2018/0253837 | A1 * | 9/2018 | Ghesu | G06T 7/0012 |
| 2019/0082990 | A1 * | 3/2019 | Poltorak | A61B 5/377 |
| 2019/0159712 | A1 * | 5/2019 | Marks | A61B 5/055 |
| 2019/0385306 | A1 * | 12/2019 | Kim | G06F 17/15 |

FOREIGN PATENT DOCUMENTS

| | | | | |
|---|---|---|---|---|
| EP | 3370206 | A1 * | 9/2018 | |
| EP | 3370206 | A1 | 9/2018 | |
| EP | 3828896 | A1 * | 6/2021 | ............... G06N 3/02 |
| WO | WO-2013001410 | A2 * | 1/2013 | |
| WO | WO 2013001410 | A2 | 1/2013 | |
| WO | WO-2016059775 | A1 * | 4/2016 | |
| WO | WO-2016090093 | A1 * | 6/2016 | ........... A61F 2/5046 |
| WO | WO-2017096353 | A1 * | 6/2017 | |
| WO | WO-2019173237 | A1 * | 9/2019 | |
| WO | WO-2020173573 | A1 * | 9/2020 | |

OTHER PUBLICATIONS

Extended European Search Report dated Mar. 13, 2020.

* cited by examiner

PATIENT FOLLOW-UP ANALYSIS

PRIORITY STATEMENT

The present application hereby claims priority under 35 U.S.C. § 119 to European patent application number EP19212054.1 filed Nov. 28, 2019, the entire contents of which are hereby incorporated herein by reference.

FIELD

Example embodiments generally relate to the follow-up analysis of patient data, such as medical image data.

BACKGROUND

Follow-up reading and change assessment is important when deriving medical diagnosis from medical images acquired by medical image acquisition modalities, such as x-ray device, ultrasound devices, CT or MR scanners. Radiologists generally rely not only on the latest available images but on the whole history in their decision making. This history might include multiple medical image data sets obtained on the same patient (on the same body part of the patient) at different times and, usually, with different medical imaging techniques. By keeping track of such follow-up examinations, a change in medical findings over time can be determined thereby generating valuable insights for deriving a proper medical diagnosis. The change of the findings can for example indicate, whether a tumor is growing or a stenosis worsening and immediately impacts on therapy decisions.

Especially three-dimensional image acquisition technologies, such as CT or MR, result in a large number of images. Accordingly, it becomes very time consuming to navigate through the images to identify the image or the small number of images relevant for the medical finding in prior image scans to be able to determine changes in medical findings over time. The procedure becomes even more involved if data acquired with different imaging parameters or even different imaging modalities shall be compared as these data sets are usually not aligned very well. By consequence, the same or similar anatomical features of the subject will appear at different positions in follow-up image data sets. Further difficulties arise from "normal" anatomical changes coming from the breathing motion or other "healthy" anatomical differences of the patient which are always present and mask potentially relevant medical findings.

To assist radiologists in this task, different methods of three-dimensional (image) registration of image volumes have been devised. Such methods essentially derive a coordinate transformation between the coordinate systems of the follow-up image data sets based upon raw image data. As these methods typically rely on various image processing steps to facilitate a spatial co-registration and matching corresponding anatomies in both data sets, they require the two image volumes to be registered to be available locally.

SUMMARY

In practice, the inventors have discovered that this cannot always be ensured, however. To start with, medical image data is typically very large. Taking a chest CT-data set as a typical example, one can safely assume that a single scan takes up more than 100 MB of disk space. Holding such data sets readily available for a possible later comparison would require very high storage capacities—with the consequence that required data oftentimes has already been discarded until needed for follow-up reading.

What is more, the inventors have discovered that the new and the previous image volumes are often stored at different storage locations. The image volume for the newly performed examination might be available locally at the reading computer system of the radiologist, whereas the previous image volume is stored in a central image database, for example, of a Picture Archiving and Communication System (PACS). Under such circumstances, access rights to the image database can be an issue and transmitting such large data files might still take significant lengths of time. This is even more so if the previous image volume is stored at a remote storage location with a poor or no network access at all.

The inventors have discovered that the situation is even worse if the image registration shall be offered in the form of a cloud service. Here, data security and privacy guidelines often severely limit access rights of cloud service providers to local databases storing medical information. In turn, archiving complete image data sets in a cloud platform for follow-up reading often is also no sustainable option as this would require huge data storage capacities and likewise raises important patient data privacy concerns.

Therefore, at least one embodiment of the present invention provides a computer-aided diagnosis tool which supports a user/physician/radiologist/pathologist in deriving a medical diagnosis from medical image data, in particular, by implementing improved automated follow-up reading functionalities. In this regard, at least one embodiment of the present invention provides an improved computer-implemented method which can be readily implemented in a distributed environment, seamlessly integrates into existing clinical workflows, and improves the availability of comparative data for follow-up reading. Furthermore, the inventors have discovered that it is desired to provide methods (and associated systems) that more readily comply with existing data privacy regulations, that can be flexibly applied to medical image data from various sources, and that reduce the amount of data that needs to be held available.

Embodiments are directed to a method for comparing follow-up medical examinations, a corresponding system, a corresponding computer-program product and a computer-readable storage medium. Alternative and/or preferred embodiments are object of the claims.

In the following, the technical solution according to at least one embodiment of the present invention is described with respect to the claimed apparatuses as well as with respect to the claimed methods. Features, advantages or alternative embodiments described herein can likewise be assigned to other claimed objects and vice versa. In other words, claims addressing the inventive method can be improved by features described or claimed with respect to the apparatuses. In this case, e.g., functional features of the method are embodied by objective units or elements of the apparatus.

According to an embodiment, a computer-implemented method for comparing follow-up medical examinations (or follow up medical image data) is provided. The method comprises several steps. A first step is directed to receiving a medical image data set showing a body part of a patient at a first time. That followed, at least one reference data set associated to the image data set is retrieved from a database, wherein the reference data set comprises reference biometric data having been extracted from a reference image data set depicting the body part of the patient at second time different than the first time.

Thereby, the reference biometric data define locations of anatomies of the body part in the reference image data set. A next step is directed to extracting, from the image data set, biometric data which define locations of anatomies of the body part in the received image data set and which at least partly correspond to the reference biometric data previously extracted from the reference image data set an comprised in the reference data. Next, a registration of the reference data set with image data set is performed on the basis the reference biometric data and the extracted biometric data, based upon which the image data set is then compared with the reference data set.

According to another embodiment, a computer-implemented method for comparing follow-up medical image data is provided which comprises a plurality of steps. A first step is directed to receiving a medical image data set showing a body part of a patient at a first time followed by a step of retrieving, from a database, a reference data set associated to the image data set, wherein the reference data set has been extracted from a reference image data set depicting the body part of the patient at second time different than the first time, and the reference data set comprises a plurality of position-specific reference values respectively relating to locations in the reference image data set. A further step is directed to extract, from the image data set, an extracted data set comprising a plurality of position-specific extracted values which respectively relate to locations in the body part of the image data set and which at least partly corresponds to the reference data set. A further step is directed to perform a registration of the reference data set with the extracted data set by registering at least a part of the reference data set with at least a part of the extracted data set. Yet, a further step is directed to compare the reference data set with the extracted data set based upon the registration, in particular by quantifying a change from the reference data set to the extracted data set.

According to another embodiment, a system for comparing follow-up medical examinations is provided which comprises an interface unit and a computing unit. The interface unit is configured for receiving, from a site external to the system, medical image data sets, and for communicating with a database storing a plurality of reference data sets having been extracted from medical image data sets. The computing unit is configured to receive, via the interface unit, an image data set depicting a body part of a patient at a first time, and to retrieve, from the database, at least one reference data set associated to the image data set. Thereby, the reference data set comprises reference biometric data having been extracted from a reference image data set depicting the body part of the patient at second time different than the first time, wherein the reference biometric data defines locations of anatomies of the body part in the reference image data set. The computing unit is further configured to process the image data set, so as to extract, from the image data set, biometric data which define locations of anatomies of the body part in the image data set and which at least partly correspond to the reference biometric data, to perform a registration of the reference data set with image data set on the basis the reference biometric data and the extracted biometric data, and to compare the image data set with the reference data set based upon the registration.

According to another embodiment, the present invention is directed to a computer program product comprising program elements which induce a computing unit of a system for comparing follow-up medical examination results to perform the steps according to an embodiment of the method, when the program elements are loaded into a memory of the computing unit.

According to another embodiment, the present invention is directed to a computer-readable medium on which program elements are stored that are readable and executable by a computing unit of a system for comparing follow-up medical examinations, in order to perform steps of an embodiment of the inventive method, when the program elements are executed by the computing unit.

Another embodiment is directed to a computer-implemented method for comparing follow-up medical examinations, the computer-implemented method comprising:
  receiving a medical image data set showing a body part of a patient at a first time;
  retrieving, from a database, at least one reference data set associated to the image data set, wherein the at least one reference data set includes reference biometric data extracted from a reference image data set depicting the body part of the patient at a second time, different from the first time, the reference biometric data defining locations of one or more anatomies of the body part in the at least one reference image data set;
  extracting, from the image data set, extracted biometric data defining locations of one or more anatomies of the body part in the image data set and at least partly corresponding to the reference biometric data;
  performing a registration of the at least one reference data set with the image data set based upon the reference biometric data and the extracted biometric data;
  comparing the image data set with the at least one reference data set based upon the registration performed.

Another embodiment is directed to a computer-implemented method for comparing follow-up medical examinations, the method comprising:
  receiving a medical image data set showing a body part of a patient at a first time;
  retrieving, from a database, a reference data set associated to the image data set, the reference data set having been extracted from a reference image data set depicting the body part of the patient at second time, different than the first time, and the reference data set including a plurality of position-specific reference values respectively relating to locations in the reference image data set;
  extracting, from the image data set, an extracted data set comprising a plurality of position-specific extracted values respectively relating to locations in the body part of the image data set, and at least partly corresponding to the reference data set;
  performing a registration of the reference data set with the extracted data set by registering at least a part of the reference data set with at least a part of the extracted data set; and comparing the reference data set with the extracted data set based upon the registration.

Another embodiment is directed to a system for comparing follow-up medical examinations, comprising:
  a computing unit, configured to:
    receive an image data set depicting a body part of a patient at a first time;
    retrieve, from a database, at least one reference data set associated to the image data set, the at least one reference data set including reference biometric data extracted from a reference image data set depicting the body part of the patient at a second time, different from the first time, and the reference biometric data defining locations of anatomies of the body part in the reference image data set;

process the image data set, so as to extract, from the image data set, biometric data defining locations of one or more anatomies of the body part in the image data set and at least partly corresponding to the reference biometric data;

perform a registration of the at least one reference data set with the image data set based upon the reference biometric data and the extracted biometric data; and compare the image data set with the at least one reference data set based upon the registration.

Another embodiment is directed to a non-transitory computer program product storing program elements which induce a computing unit of a system for comparing follow-up medical examinations to perform the method of an embodiment when the program elements are loaded into a memory of the computing unit.

Another embodiment is directed to a non-transitory computer-readable medium storing program elements, readable and executable by a computing unit of a system for comparing follow-up medical examinations, to perform the method of an embodiment, when the program elements are executed by the computing unit.

BRIEF DESCRIPTION OF THE DRAWINGS

Characteristics, features and advantages of the above described invention, as well as the manner they are achieved, become clearer and more understandable in the light of the following description and embodiments, which will be described in detail with respect to the figures. This following description does not limit the invention on the contained embodiments. Same components or parts can be labeled with the same reference signs in different figures. In general, the figures are not drawn to scale. In the following.

DETAILED DESCRIPTION OF THE EXAMPLE EMBODIMENTS

Figure 1:
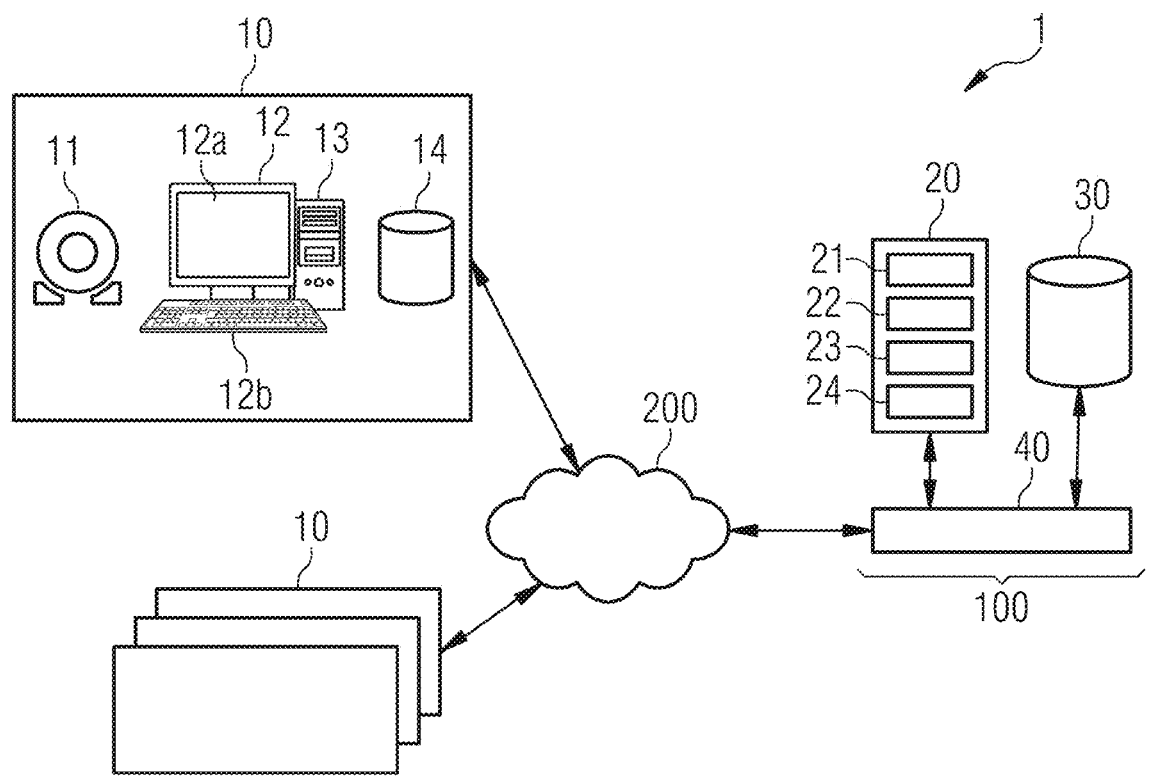
FIG. 1 depicts a distributed environment for comparing follow-up medical examinations according to an embodiment.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without subdividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to an embodiment, a computer-implemented method for comparing follow-up medical examinations (or follow up medical image data) is provided. The method comprises several steps. A first step is directed to receiving a medical image data set showing a body part of a patient at a first time. That followed, at least one reference data set associated to the image data set is retrieved from a database, wherein the reference data set comprises reference biometric data having been extracted from a reference image data set depicting the body part of the patient at second time different than the first time. Thereby, the reference biometric data define locations of anatomies of the body part in the reference image data set. A next step is directed to extracting, from the image data set, biometric data which define locations of anatomies of the body part in the received image data set and which at least partly correspond to the reference biometric data previously extracted from the reference image data set an comprised in the reference data. Next, a registration of the reference data set with image data set is performed on the basis the reference biometric data and the extracted biometric data, based upon which the image data set is then compared with the reference data set.

The (medical) image data sets (i.e., the reference image data set and the received image data set) may relate to two-dimensional data sets providing two dimensions in space. Further, the images data sets may relate to three-dimensional data sets providing three dimensions in space (in other words, the medical image data sets may thus relate to volumetric image data also designated as medical image volume). Still further, the image data sets may relate to time series of two- or three-dimensional image data sets. The image data sets depict a body part of a patient in the sense that they contain two- or three-dimensional image data of the patient's body part (i.e., the reference medical image data set and the medical image data set as introduced above image data sets may depict the same body part of the same patient).

The medical image data sets may, for example, be in the form of an array of pixels or voxels. Such arrays of pixels or voxels may be representative of intensity, absorption or other parameter as a function of two- or three-dimensional position, and may, for example, be obtained by suitable processing of measurement signals obtained by a medical imaging modality. A medical imaging modality corresponds to a system used to generate or produce medical image data sets. For example, a medical imaging modality may be a computed tomography system (CT system), a magnetic resonance system (MR system), an angiography (or C-arm X-ray) system, a positron-emission tomography system (PET system), an ultra-sound-imaging system or the like. Specifically, computed tomography is a widely used imaging method and makes use of "hard" X-rays produced and detected by a specially rotating instrument. The resulting attenuation data (also referred to as raw data) is presented by a computed analytic software producing detailed images of the internal structure of the patient's body parts. The produced sets of images are called CT-scans which may constitute multiple series of sequential images to present the internal anatomical structures in cross sections perpendicular to the axis of the human body.

Magnetic Resonance Imaging (MRI), to provide another example, is an advanced medical imaging technique which makes use of the effect magnetic field impacts on movements of protons. In MRI machines, the detectors are antennas and the signals are analyzed by a computer creating detailed images of the internal structures in any section of the human body. Accordingly, the depicted body part of the patient in general will comprise a plurality of anatomies and/or organs. Taking a chest image as an example, reference and follow-up image data may show lung tissue, the rib cage, lymph nodes and others.

While the received (medical) image data set has been taken at an examination at a first time, the reference (medical) image data set relates to an examination taken at a second time different than the first time. The second time may be hours, days, weeks, months, or years after or before the first time. Further, there may be intervening scans or procedures between the first time and the second time. In an embodiment, the second time precedes the first time, so that the received medical image data set may be conceived as relating to a follow-up examination with respect to the reference medical image data set. In an embodiment, the image data set has been acquired using the same medical imaging modality with the same or similar settings and parameters as the reference image data set. According to another embodiment, the image data set has been acquired using different medical imaging modalities. For instance, the reference image data set may have been acquired using a CT system, while the received image data set has been acquired using an ultra-sound system.

"Receiving" may mean that the image data set is provided by a user by way of an upload. As an alternative, the image data set may be received with the help of another computer-implemented method via an automated workflow outside of the presently claimed method. For instance, it is conceivable that the image data set is provided by a computer aided diagnosis system that automatically or semi-automatically selects image data sets for follow-up analysis according to the claimed method. In any case, the step of receiving triggers the subsequent processing steps and, if initiated by a user, may be seen as an implicit user request for performing the follow-up image analysis according to the subsequent steps. While "receiving" may be conceived as a passive step, the ensuing step of "retrieving" (as well as the further subsequent steps) may be conceived as active steps in which the method actively looks for appropriate reference data set(s) for follow-up reading.

The database may be a database of reference data sets from various patients for the comparison of follow-up medical data sets according to the invention. It may include any storage medium or organizational unit for storing and accessing reference data sets. The database may include a plurality of individual memory units and repositories and may, in particular, include distributed data architectures. The database may include a variety of data records accessed by an appropriate interface to manage delivery of reference data sets. The database may be a local database accessible by the method. The database may be located at the same site from which the medical image data set is received. Further, the database may be embodied as a cloud storage facility and may thus provide a platform for centrally archiving reference data sets from a plurality of institutions (or sites or users).

The reference data set constitutes the reference or baseline data derived from a reference examination for comparison with the submitted image data. Being "associated to the received image data set" may mean that both data sets (i.e., the image data set and the reference data set) belong to the same patient but represent data taken at different points in time. The association may be embodied by a data identifier assigned to both data sets and unambiguously linking the two data sets. This data identifier may be an accession number, a patient's ID, a patient's name and so forth.

The step of "retrieving" may be conceived as a step of automatically querying the database for reference data sets based upon the received image data set. Noteworthy, the step is not limited to retrieving exactly one reference data set. Rather, there may be additional reference data sets besides the at least one reference data set mentioned in the step. Accordingly, the step, in other words, comprises retrieving at "least one" reference data set or "one or more" reference data sets each having been taken at different second times, respectively. All of the retrieved reference data sets may be subjected to the same processing steps, i.e., the extraction of corresponding information from the received image data set, the registration with the image data set (and, optionally, the other retrieved reference data sets) and the comparison with the received image data set (and, facultatively, the other retrieved reference data sets). Accordingly, the method also allows for the systematic comparison of image data sets with a plurality of reference data sets and thus enables tracking a disease or health progression over a plurality of follow-up examinations.

While the medical image data sets primarily comprise image data, the reference data set does primarily comprise data which has been extracted from medical image data by one or more image processing steps. While all or part of the original image data might still be comprised in the reference data sets, it is preferred that the reference data sets comprise the extracted data in lieu of the underlying complete image data set.

Specifically, the reference data set comprises reference biometric data which has been extracted from the reference medical image data set. Biometric data define the location of anatomies in the body part as depicted in the (reference) image data sets. Biometric data may relate to biological meaningful points, regions, contours, lines, and so forth in which correspondences (e.g., in the form of homologous parts) between different images data sets of the body part under examination are preserved. In other words, the biometric data relates to distinctive, measurable geometric identifiers definable in the depicted body part. Specifically, biometric data may be vertices, anchor points, control points, sites, profile points, 'sampling' points, nodes, markers, fiducial markers, points in a shape that are located according to some mathematical or geometrical property, fixed points, markers, features or structures that can be defined in the body part depicted in the (reference) image data sets. Although the locations of the biometric data are given in the coordinates of the underlying image data set, the existence of the corresponding features is invariant between image data sets and just depends on the underlying body part.

Accordingly, such biometric data can be used to describe the positional relationship of findings, observations, anatomies and organs inside the body parts independent of the subjective coordinate system spanned by the pixels or voxels of the medical image data set. The biometric data may be seen as invariant in the sense that each body part of the same kind contains these biometric data points—albeit at different locations in the medical image data sets. In other words, the biometric data is at least to some extent universal in the sense that every body part of the same kind should possess the underlying trait.

Specifically, the biometric data may comprise one or more (anatomic) landmarks, one or more sets or meshes of landmarks, one or more anatomic (bio-)markers, one or more sets or meshes of anatomic (bio-)markers, one or more contours or segmentation masks of organs or anatomies comprised in the body part, one or more surface maps or meshes of organs or anatomies comprised in the body part, wherein a surface mesh may be conceived as a set and/or collection of points describing the surface of an object. Since the existence or presence of the biometric data is invariant when comparing different medical image data sets, they may be used as reference points or benchmarks for comparing the outcome of follow-up examinations and provide an excellent basis for the registration of two data sets.

Such (reference) biometric data may be extracted from the reference medical image data set using several known methods. For the extraction of one or more anatomic landmarks from medical image data sets reference is made to US 2018/0 005 083 A1 and EP 3 370 206 A1, for instance, the contents of which are included herein by reference.

In order to compare the retrieved reference data set with the received follow-up-medical image data set, the follow-up medical image data set in a next step is to be processed so as to extract, from the follow-up medical image data, data corresponding to the reference data set. In other words, this means extracting from the received image data set biometric data at least partly corresponding to the reference biometric data. The extraction of the biometric data from the image data set may rely on the same or on different procedures as compared to the extraction of the reference biometric data. As the biometric data relates to generic geometric identifiers, it is in general not crucial which method was actually used for their extraction.

"At least partly corresponding" in this context may mean that at least a part of the reference biometric data relates to the same biometric information as at least a part of the newly extracted biometric data. For instance, the reference biometric data may comprise a first set of anatomic landmarks or surface meshes and the extracted biometric data may comprise a second set of landmarks or surface meshes, wherein the first and second sets at least partially overlap. It should be noted in this context that the reference biometric data and the extracted biometric data are extracted from different medical image data sets which may have different imaging parameters or altogether stem from different imaging modalities. By consequence, the derivable biometric information may naturally differ to some extent so that a one-to-one correspondence of the biometric information is only rarely achievable anyway. However, suchlike partial correspondence is generally sufficient for a registrationbased as this particular method is generally very capable also when dealing with spare data sets (in contrast to other techniques such as correlation-based algorithms).

With the reference biometric data and their extracted counterparts at hand, a registration can be performed, where the corresponding parts of the retrieved reference biometric data and the extracted biometric data are registered with one another. If anatomic landmarks are considered as examples for information comprised in the biometric data, the registration may be based on a set of pairs of corresponding anatomic landmarks, each pair of corresponding anatomic landmarks comprising a first anatomic landmark extracted from the reference image data set and a corresponding second anatomic landmark extracted from the uploaded/received image data set. The registration may comprise calculating a (global) transformation function (or transformation matrix) which maps the positions in the received image data set to corresponding positions in the reference (image) data set and minimizes the spatial distances of the locations of the biometric data for the two medical image data sets.

The transformation function may be conceived as extrapolating the displacements traceable for the reference and extracted biometric data to the entire image volume as covered by the image data set and the reference (image) data set. The transformation function be may be based on rigid, affine, non-rigid transformations, and/or any combination thereof. Further, the calculation of the transformation function may involve using a deformation model for softtissue deformation as exemplified by the Navier-Cauchy equation. The transformation function derived in the registration step not only provides information of how the coordinates of biometric data in one image data set translate into the coordinates of another image data set, but also provides an indication of how the entire two- or three-dimensional coordinate systems of reference and follow-up images locally transform.

Accordingly, with the registration (i.e., the derived transformation function), the received image data set can be directly compared to the reference data set, as, for instance, any local information (e.g., pertaining to a localized observation in the reference image data set) as comprised the reference data set can be transformed into the coordinate system of the received medical image data set and vice versa. This makes is possible to match spatially corresponding information and quantify any changes on that basis (for that matter, the step of comparing may comprise, matching spatially corresponding information in the image data set and the reference data set and quantify any change on that basis).

In summary, the method steps as introduced above synergistically contribute to a method facilitating an efficient comparison of follow-up medical image data (medical examinations) thereby improving the process of follow-up reading. Accordingly, a method is provided that assists the user in providing a medical diagnosis by processing physiological measurements. Thereby, the method allows to compare in medical image data sets and thereby helps to determine disease progressions, treatment responses, and the like. Basing the co-registration of follow-up medical images on a registration based on biometric data (e.g., in the form of anatomic landmarks) and not on traditional two- or three-dimensional image registration has a two-fold advantage. On the one hand, the biometric data as introduced above provides generic and universal reference points for the registration. This is because, the biometric data does not—or at least not primarily—depend on imaging parameters but on physiological properties of the body part under consideration. This improves the comparability of results generated with different imaging parameters and readily enables integrating results from different modalities. Since the usage of biometric data allows for a standardized way to compare follow-up medical images, the procedure seamlessly integrates into existing workflows and requires fewer manual interactions.

In this respect, the automatic retrieval of the reference data set from the database in particular decreases the workload of the user, since he does not need to provide the reference data sets by himself. What is more, through the automatic retrieval, it can be more reliably ensured that no relevant data for comparison is missed. On the other hand, the method enables to considerably decrease the amount of data that needs to be handled in connection with the reference data. By consequence, more reference data sets can be held available which increases the likelihood that a suited reference data set can actually be retrieved. Since the reference data sets are held available in an already processed format, only the newly received image data set needs to be processed. This reduces the processing times and the required computational power and more swiftly enables the comparison to a plurality of reference data sets at once. Moreover, also the data traffic and thus network latencies can be reduced. What is more, the retrieval from a designated database makes it more readily possible to grant the required data access rights and obey existing data privacy regulations.

According to an embodiment, the step of performing the performing the registration comprises: selecting a biometric region which is common to the biometric data and the reference biometric data as a region which is a standard for registering the medical image data and the reference data set; and a registration step of performing a registration (preferably rigid, non-rigid, affine or any combination thereof) using the biometric region as the registration standard.

According to an embodiment, the step of performing the registration comprises determining corresponding biometric information in reference and follow-up biometric data, and using the corresponding biometric information for performing the registration.

According to an embodiment, the step of performing the registration comprises analyzing the biometric data and the reference biometric data so as to determine corresponding data points in the biometric data and the reference biometric data, and a registration step of performing a registration (preferably rigid, non-rigid, affine or any combination thereof) for the medical image data set and the reference data set, using the corresponding data points.

By determining the corresponding data points and/or the biometric region and/or the corresponding biometric information, it can be ensured that only corresponding data is used for the registration. In doing so the registration can be rendered more efficient as computation times may be shortened and the results are likely more accurate. Further, this improves the compatibility of different data sets, which may, for instance, show considerably different imaging windows or relate to results from different imaging modalities. Corresponding data relates to data that is common in both data sets. The corresponding data may, for instance, relate to the same anatomic landmarks, the same anatomic surface meshes or the like.

According to an embodiment, the reference data set further comprises one or more reference medical findings having been extracted from the reference image data set, the reference medical findings being respectively associated to locations in the reference image data set, wherein the step of extracting further comprises extracting, from the image data set, one or more medical findings associated to locations in the image data set, wherein the step of comparing comprises comparing the extracted medical findings with the reference medical findings, in particular, by quantifying a change in the medical findings.

The (reference) medical findings may be seen as information about a physiological or pathological feature or observation at a given location in the (reference) medical image data sets. The information comprised in the medical findings may be numerical information. For instance, it may comprise the volume, cross-section, circumference, diameter and the like of a lesion, nodule, mass or other pathologically relevant feature in the body part as extracted/measured from the respectively underlying image data set. Moreover, it may comprise secondary information such as degrees of malignancy, already established growth or shrinkage rates, values quantifying observables such as a state of the contour (either smooth or spiculated), a degree of calcification or fat deposition, or degree of solidity. Moreover, the information comprised in the medical findings may be in the form of cut-outs or clippings from the (reference) image data sets of pathological relevant areas (i.e., the medical findings may comprise image data as well) or in the form of a segmentation in the sense of a form of a lesion. In addition, the information may be semantic information describing the medical findings information with words. According to an embodiment, the ensemble of medical findings as comprised in the reference data set may be a structured report in a human readable format, for instance, in the form of a list. The location of the (reference) medical findings may generally be given in the coordinate system of the underlying image data set.

Several established methods and approaches exist for the (automated and/or semi-automated) extraction of one or more of the abovementioned medical findings from image data sets. These approaches may, for instance, rely on traditional image processing techniques such as image segmentation, pattern or feature recognition and the like and/or may employ machine learning.

With the reference data sets already comprising medical findings, it is no longer required to calculate this information anew when comparing the uploaded image data set to the corresponding reference data set. By consequence, the computation times can be decreased. At the same time, this enables storing all relevant information for follow-up reading in a very condensed form. Compared to (raw) medical image data, this brings about a considerable decrease in the amount of data that needs to be exchanged and stored.

Furthermore, it also becomes more readily possible to anonymize the reference data and, thus, store this information in externally accessible databases or in the cloud.

According to an embodiment, it is also conceivable that the biometric data itself contains one or more of the abovementioned medical findings as their relative location within the body part may, as the case may be, as well be invariant from examination to examination.

The usage of medical findings as biometric data essentially means that the same information may be used twice, further increasing the effectivity of the method and decreasing the amount of data required.

According to an embodiment, the step of comparing may comprise transforming the locations of the reference medical findings into the coordinate system of the extracted medical findings or vice versa using the registration (or, in particular, the calculated transformation function).

The coordinate transformation of the findings' locations into the respective other coordinate system may also be designated as a step of aligning or co-aligning the extracted medical findings and the reference medical findings using the registration (or, in particular, the calculated transformation function). The step of aligning facilitates the identification of corresponding findings and thus improves the follow-up reading.

According to an embodiment, the step of comparing may comprise matching (at least part of) the extracted medical findings with (at least part of) the reference medical findings based upon the registration and/or the transformation function and/or the step of aligning.

The matching may be conceived as a step of identifying pairs of associated findings in the extracted and reference medical findings based upon the registration. In an example embodiment, for each pair of a finding in the reference data set and a finding extracted from the received image data set, a probability may be calculated that the two findings describe the same pathology or medical observation, for example taking into account the proximity of transformed (aligned) locations of the findings, whether they are of the same type and how similar other parameters are.

According to an embodiment, the step of comparing may comprise quantifying a change from the extracted medical findings to the reference medical findings based upon the step of comparing and/or the step of aligning and/or the step of matching.

The automatic determination of a change in the medical findings makes it more readily possible for a user to follow-up the current status of the case, on a disease progression, or treatment responses.

According to an embodiment, the reference biometric data and the biometric data respectively comprise on or more anatomic landmarks (preferably a set of anatomic landmarks), and/or one or more surface meshes of anatomies comprised in the body part.

The anatomic landmarks may, for instance for the chest area, be selected from the group comprising: aortic root and arch, artery bifurcations (the bifurcation of brachiocephalic, carotid or subclavian arteries, the celiac trunk, the renal bifurcation), carina bifurcation, the top of left and right kidney, top of left and right lung, center and top of the liver, pancreas, tip of the sternum, vertebral bodies. The surface meshes may be selected from the group comprising: lung lobes (left upper and lower, right upper, middle and lower), heart, aorta, vertebrae.

Anatomic landmarks or surface meshes are universal to body parts and/or anatomies. The usage of these data points makes any information associated thereto readily comparable across different examinations, treatment stages, imaging parameters, imaging modalities and also patients (if required). Moreover, there exists a plethora of well-established and standardized methods of automatically extracting anatomic landmarks and/or surface meshes from medical image data which further improves the interchangeability of the results. Further, anatomic landmarks and surface meshes are ideally suited as anchor points for registration as they typically capture the overall anatomic configuration of a body part very well. Taking the set of anatomic landmarks listed above as an example (or even just a subset of them), this give a comprehensive picture of the overall displacements and deformations from one image data set of a patient to another. Noteworthy, the biometric data may combine different species of biometric information. For instance, the biometric data may comprise a set of anatomic landmarks associated to the chest area and a one or more surface meshes directed to the heart and a segmentation mask associated to the lung. Dependent on the case at hand, such combination of "orthogonal" information may provide a very good picture about the deformations and displacements in follow-up image data sets.

According to an embodiment, the step of retrieving comprises extracting a data identifier from the received image data set, and querying the database for the reference data set using the data identifier.

In other words, the medical image data set and the reference data set may be interconnected via a structural association in the form of data identifiers so that each medical image data set is unambiguously related to one or more corresponding reference data sets. The data identifier may be a (unique) electronic data identifier or any other suitable electronic tag. Specifically, the data identifier may comprise the patient's ID or an accession number. The data identifier can also comprise a hash of the data mentioned before and/or any combination thereof. The data identifier serves as a link between the image data set and the reference data set. According to an embodiment, all data pertaining to a specific patient may bear the same data identifier. Accordingly, an association between a received image data set and one or more reference data sets can be established based on a comparison or matching the data identifiers. In practice, the unique identifier may be encoded in the header of the medical image data set, for instance. According to an embodiment, the data identifiers are anonymized so that no personal patient information (such as the patient's name) can be derived therefrom.

The use of data identifiers is beneficial for swiftly querying the database for the correct reference data sets corresponding to the received image data set. Accordingly, this improves the integration of the method into existing workflows and ensures that all relevant reference data sets can be found.

According to an embodiment, the step of retrieving comprises, retrieving from the database one or more candidate reference data sets, providing the one or more candidate reference data to a user for selecting, from the candidate reference data, at least one user-selected reference data set, receiving the user selection, and using the user-selected at least one reference data set as the reference data set.

There may be cases, where there are more than one possible reference data set for an image data set in the database. The available reference data sets may relate to different examination time and/or image data acquired with different imaging modalities, for instance. One option in this regard would be using all of the available reference data sets for the ensuing registration and comparison. Another option would be automatically selecting the one or more most probable reference data sets (based on one or more selection criteria—see below). Yet another option is the interactive selection according to the above embodiment, where the candidate reference data sets are presented to the user (who submitted the image data set in the first place). In doing so, the method can specifically adapt to the needs of the user, as he or she may select which of the available reference data sets constitute the most interesting ones for the comparison.

According to an embodiment, the step of retrieving comprises: setting (or providing) one or more selection criteria for retrieving the reference data and retrieving the reference data based on the selection criteria. Thereby, the selection criteria preferably are based on at least one of: an indication of the imaging modality used for acquiring the received image data and/or the reference data set, a time window between the first and second time points, an indication of an identity of a patient (e.g., in the form of the aforementioned data identifier), an indication whether a comparison to a prior or follow-up examination is desired for the received image data set, an indications of one or more prior selection of reference data sets (of a user), and/or any combination of the aforesaid. Indication in this context may relate to an appropriate data identifier such as a patient ID or an electronic tag indicative of the used imaging modality and so forth.

According to an embodiment, the selection criteria may be interactively set by a user. As an alternative, the selection criteria may be set semi-automatically (e.g., in terms of an initialization with default values) or automatically for users who need more assistance. The time window may be defined as the maximal period of time between the first and second times. The prior selections may relate to prior uses of reference data sets for comparison or prior user selections. Information for applying the selection criteria may be recorded in the reference data sets and may be extracted therefrom. Further pieces of information may be comprised in the image data sets and may be extracted therefrom. For instance, the information may be adhered to the body of the medical image data set or reference data sets as metadata, e.g., in the form of a header. Accordingly, retrieving the reference data sets based on the selection criteria may comprise accessing and/or reading and/or processing the image data sets and the reference data sets for extracting information corresponding to one or more of the selection criteria.

The selection criteria can be conceived as a filter for narrowing the search for appropriate reference data sets. By consequence, applying the selection criteria means that more meaningful results can generated in shorter time.

According to an embodiment the method further comprises the step of compiling (or, in other words, generating) a further reference data set using the extracted biometric data, and forwarding the further reference data set to the database for storing it in the database. Further, the method may comprise storing the further reference data set in the database.

According to an embodiment, the further reference data set is compiled using the DICOM format. According to a further embodiment, also the reference data set(s) retrieved from the database are formatted according to the DICOM format. DICOM (=Digital Imaging and Communications in Medicine) is an open standard for the communication and management of medical imaging information and related data in healthcare informatics. DICOM may be used for storing and transmitting medical images and associated information enabling the integration of medical imaging devices such as scanners, servers, workstations, printers, network hardware, and picture archiving and communication systems (PACS). It is widely adopted by clinical syndicates, hospitals, as well as for smaller applications like doctors' offices or practices.

A DICOM data object consists of a number of attributes, including items such as patient's name, ID, etc., and also special attributes containing the image pixel data and metadata extracted from the image data. The latter can be used for the biometric data and/or medical findings according to an embodiment of the invention.

By including the data extracted from the received medical image data set into the database alongside the already existing reference data sets, the shared knowledge comprised in the system is enhanced and the comparison of follow-up medical image data is rendered more efficient for subsequent queries. The usage of the DICOM data format improves the compatibility of the method existing clinical workflows and equipment.

According to an embodiment, the database is configured as a cloud platform.

Realizing the database as a cloud platform has the advantage that it can be more readily accessed from various sites by various users. This may have the benefit that the usability and build-up of the knowledge database is fostered.

According to an embodiment, the database is part of a Picture Archiving and Communication System (PACS)—which may be realized as a cloud storage or as a local or spread storage.

Relying on a PACS-system for storing the reference data sets is beneficial in that existing infrastructure can be used which may facilitate implementation and decrease costs.

According to an embodiment, the reference data sets are anonymized, or, in other words, do not comprise any personal information pertaining to the underlying patient.

"Anonymized" may mean that the reference data sets do not reveal or contain any personal information from which the patient can be directly identified (i.e., patient's name, address, photographs and the like). Instead, the data may be made traceable by ways of unique yet anonymized identifiers such as identification numbers. According to an embodiment, the method may further comprise the step of anonymizing the medical findings and/or the biometric data prior to archiving this information in the database. The step of anonymizing may comprise filtering out any personal information with which the patient can be directly identified.

By anonymizing the data, it can be safely ruled out that the information contained in the medical findings and/or the biometric data can be traced back to the corresponding patient which is beneficial when dealing with questions of personal data privacy.

According to an embodiment, the registration of the biometric follow-up data with the reference biometric data is based on a rigid and/or affine and/or non-rigid registration and/or any combination thereof.

A rigid registration in this context may comprise a registration in which the coordinates of data points in one data set (e.g., the extracted biometric data) are subject to rotation and translation in order to register them to another data set (e.g., the reference biometric data). An affine registration in this context may comprise a registration in which the coordinates of data points in one dataset are subject to rotation, translation, scaling and/or shearing in order to register them to the corresponding data points in another dataset. Thus, a rigid registration, which only comprises translations and rotations, may be considered to be a particular type of affine registrations.

Non-rigid registrations, by contrast, allow 'elastic' transformations and can thus provide different displacements for each data point of the data sets to be registered and can, for example, use non-linear transformations, in which the coordinates of data points in one dataset are subject to flexible deformations in order to register the data set to another data set. (Non-linear) transformations may in some cases be defined using vector fields such as warp fields, or other fields or functions, defining an individual displacement for each data point in a three-dimensional data set. For more detailed information about image registration, reference is made to US 2011/0 081 066 and US 2012/0 235 679, the contents of which are included in this application by reference.

According to an embodiment, the method further comprises the steps of generating (calculating), based upon the step of comparing, a result, and forwarding the result to a user and/or archiving the result in a database. Thereby the result is preferably provided in the form of a structured medical report, one or more trending graphs, e.g., depicting changes of findings over one or more follow-up examinations, and/or a visualization viewable by a user.

According to a further embodiment, the method further comprises the steps of calculating (generating) a result based upon the quantified change in the medical findings, and forwarding the result to a user and/or storing the result in a database. Thereby, the result is preferably being in the form of one or more trending graphs illustrating the quantified change in medical findings, a structured medical report comprising indications of the quantified change in medical findings, preferably in the form of one or more DICOM SR objects, and/or a visualization viewable by a user visualizing the quantified change in medical findings.

The result generation according to the abovementioned embodiments makes the information extracted during the computer assisted follow-up reading according to the invention readily accessible for a user and therefore improves the usability of the method. What is more, the results can be more readily archived for later use.

According to an embodiment, the visualization may be of the form of an assistance image comprising a rendering of the received image data set with the change in medical findings highlighted.

By providing the user with a rendering of the submitted image data set with the change highlighted, the user can immediately infer what changes happened and where these changes occurred. This helps guiding the image reading and therefore increases the usability of the method and provides an improved assistance to the user for deriving a medical diagnosis. The rendering may rely on known rendering procedures, such as ray-casting, ray-tracing, texture-rendering, image projections or the like. The term "highlighted" in this context may mean that the pathological changes are visually enhanced in brightness, color, and/or intensity. In addition to that or as an alternative, the identified pathological changes may be highlighted using symbols. The highlighting may be effected based on information as to the identified changes, such as position, volume and amount of change. Highlighting may furthermore mean using a heatmap wherein, e.g., the amount of change is color-coded. For instance, shrinking nodules may be assigned a different color than growing nodules. The heatmap may be visualized as an overlay image on the received image data.

According to an embodiment, the medical image data set is received from a first site at a central processing system remote from the first site (and preferably being a cloud based platform), with the steps of retrieving, processing, performing, and comparing being carried out at the central processing system. According to a further embodiment, the central processing system furthermore comprises the database.

In other words, the processing of the of the medical image data set for comparing it to prior or follow-up studies is outsourced from the first site to an external central facility. This has the benefit that the first site does not need to provide the hard- and software for the processing by itself but may rely on external resources which saves costs. Moreover, it becomes readily possible to integrate knowledge from a plurality of sites, e.g., when building up the database. This is even more so if the second site is a cloud-based platform. A site in this regard may be a clinical environment, a practice, a hospital, and so forth.

The biometric data may comprise dedicated data structures characterizing geometric conformations of anatomies in image data sets such as anatomic landmarks, surface meshes and so forth. Being independent of the underlying coordinate system, information like this can be used for registration purposes and the calculation of a coordinate transformation function mapping the coordinate systems of two image data sets. However, as already mentioned, also the medical findings as such are suited to provide anchor points for registering two data sets with location-resolved information with one another (provided that there are enough pairs medical findings which in both data sets).

Accordingly, the registration may likewise be based on registering medical findings and/or combinations of medical findings and biometric data. The following embodiment makes allowance for this concept. Optional method steps as introduced and explained in connection with the previous embodiment may also be combined with the following embodiment, where applicable.

According to another embodiment, a computer-implemented method for comparing follow-up medical image data is provided which comprises a plurality of steps. A first step is directed to receiving a medical image data set showing a body part of a patient at a first time followed by a step of retrieving, from a database, a reference data set associated to the image data set, wherein the reference data set has been extracted from a reference image data set depicting the body part of the patient at second time different than the first time, and the reference data set comprises a plurality of position-specific reference values respectively relating to locations in the reference image data set. A further step is directed to extract, from the image data set, an extracted data set comprising a plurality of position-specific extracted values which respectively relate to locations in the body part of the image data set and which at least partly corresponds to the reference data set. A further step is directed to perform a registration of the reference data set with the extracted data set by registering at least a part of the reference data set with at least a part of the extracted data set. Yet, a further step is directed to compare the reference data set with the extracted data set based upon the registration, in particular by quantifying a change from the reference data set to the extracted data set.

The position-specific values respectively relate to location-resolved information extracted from underling image data information. By identifying pairs of corresponding location-resolved values, it becomes possible to register the extracted data set and the reference data set with one another and calculate a transformation function mapping the position-specific data in one data set to the position-specific data in the respective other data set. With that, it becomes possible to compare the two data sets, the reference data set and the extracted data set, and optionally quantify any changes between the extracted data and the reference data as retrieved from the database. Thereby, the reference values and the extracted values may respectively comprise one or medical findings (as introduced above) and/or biometric data (as introduced above).

According to another embodiment, a system for comparing follow-up medical examinations is provided which comprises an interface unit and a computing unit. The interface unit is configured for receiving, from a site external to the system, medical image data sets, and for communicating with a database storing a plurality of reference data sets having been extracted from medical image data sets. The computing unit is configured to receive, via the interface unit, an image data set depicting a body part of a patient at a first time, and to retrieve, from the database, at least one reference data set associated to the image data set. Thereby, the reference data set comprises reference biometric data having been extracted from a reference image data set depicting the body part of the patient at second time different than the first time, wherein the reference biometric data defines locations of anatomies of the body part in the reference image data set. The computing unit is further configured to process the image data set, so as to extract, from the image data set, biometric data which define locations of anatomies of the body part in the image data set and which at least partly correspond to the reference biometric data, to perform a registration of the reference data set with image data set on the basis the reference biometric data and the extracted biometric data, and to compare the image data set with the reference data set based upon the registration.

According to an embodiment, the system is adapted to implement an embodiment of the inventive method for comparing follow-up medical image data. The computing unit may comprise a retrieval unit configured to retrieve one or more reference data sets from a system's database or an external database. To this end, the retrieval unit may be configured to query the database and retrieve the one or more reference data sets. The retrieval unit may further be configured to extract, from the received image data set, a suitable data identifier and query the database on that basis. Further, the computing unit may comprise an image processing unit generally configured to process the received image data set. In particular, the image processing unit may be configured to extract, from the medical image data set, biometric data at least partly corresponding to the reference biometric data comprised in the reference data set. To do so, the image processing unit may be configured to read and analyze the reference biometric data and process the medical image data set on that basis. The computing unit may further comprise a registration unit configured to register the reference biometric data with the biometric data using at least one image registration. The computing unit may further comprise a results generation and visualization unit configured to compare the medical image data set with the reference data set and generate a result for displaying to a user and/or archiving in an appropriate database. The result may be in the form of a visualization (for a user), a structured report or one or more trending graphs indicating and/or highlighting the changes identified upon comparing.

The computing unit may be realized as a data processing system or as a part of a data processing system. Such a data processing system can, for example, comprise a cloud-computing system, a computer network, a computer, a tablet computer, a smartphone and/or the like. The computing unit may comprise hardware and/or software. The hardware may comprise, for example, one or more processors, one or more memories and combinations thereof. The one or more memories may store instructions for carrying out the method steps according to the invention. The hardware can be configurable by the software and/or be operable by the software. Generally, all units, sub-units or modules may at least temporarily be in data exchange with each other, e.g., via a network connection or respective interfaces. Consequently, individual units may be located apart from each other.

The interface unit may comprise an interface for data exchange with a local server or a central web server via internet connection for receiving the reference data set and/or medical image data set. The interface unit may be further adapted to interface with one or more users of the system, e.g., by displaying the result of the processing by the computing unit to the user (e.g., in a graphical user interface), selecting the reference data sets, and/or by adjusting parameters for image processing or visualization.

According to an embodiment, the system is a cloud-based platform.

According to an embodiment, the system further comprises the database which may be realized in the form of a cloud storage.

According to another embodiment, the present invention is directed to a computer program product comprising program elements which induce a computing unit of a system for comparing follow-up medical examination results to perform the steps according to an embodiment of the method, when the program elements are loaded into a memory of the computing unit.

According to another embodiment, the present invention is directed to a computer-readable medium on which program elements are stored that are readable and executable by a computing unit of a system for comparing follow-up medical examinations, in order to perform steps of an embodiment of the inventive method, when the program elements are executed by the computing unit.

The realization of the invention by a computer program product and/or a computer-readable medium has the advantage that already existing providing systems can be easily adopted by software updates in order to work as proposed by embodiments of the invention.

The computer program product can be, for example, a computer program or comprise another element next to the computer program as such. This other element can be hardware, e.g., a memory device, on which the computer program is stored, a hardware key for using the computer program and the like, and/or software, e.g., a documentation or a software key for using the computer program. The computer program product may further comprise development material, a runtime system and/or databases or libraries. The computer program product may be distributed among several computer instances.

FIG. 1 depicts a distributed environment 1 for identifying and quantifying changes in follow-up medical examinations according to an embodiment of the present invention. Environment 1 is adapted to perform the method according to one or more embodiments, e.g., as further described with reference to FIGS. 3 and 4.

System 1 comprises one or more clients 10 and a central processing system 100. Clients 10 and central processing system 100 are interfaced via a network 200. The central processing system 100 is generally configured to control and carry out the comparison of data derived from follow-up medical image data in distributed environment 1. Clients 10 may reside on one or more different local sites. Local sites may, for instance, relate to clinical or medical environments, such as hospitals or hospital groups, laboratories, medical imaging centers, clinics or practices. In the example, four clients 10 are shown for illustration. Distributed environment 1 is not limited to this number, however. In general, distributed environment 1 may comprise any number of clients 10. In particular, distributed environment 1 may also comprise only one client 10.

Central processing system 100 may generally be conceived as a server. As such, central processing system 100 may be a web server, for instance. Further, the central processing system 100 may be a cloud server or a local server as exemplified in FIG. 2. Central processing system 100 may be implemented using any suitable computing device(s) and/or software. Central processing system 100 may have a processor 20, a database 30, and an interface unit 40.

Network 200 may be realized as local area network (LAN), e.g., an intranet or a wide area network (WAN) or an internet. Further, network 200 may comprise a combination of different network examples.

Client 10 may comprise one or more imaging systems 11 for acquiring, image data sets IM, a user interface 12, a processing system 13 and a database 14 for storing medical image data sets and/or reference data sets derived therefrom.

Medical imaging system 11 is generally configured for acquiring, handling and storing medical image data sets. As such it may comprise one or more medical imaging modalities, such as a computed tomography system, a magnetic resonance system, an angiography (or C-arm X-ray) system, a positron-emission tomography system, a mammography system, a system for acquiring digital pathology images or the like. Further, the acquisition of medical image data sets through medical imaging system 11 may be from memory, e.g., from database 14.

Further, medical imaging system 11 may comprise an archive/review station (not shown) for storing imaging data sets IM. Such archive/review station may be realized as a cloud storage or, in addition to that or as an alternative, as a local or spread storage, e.g., in the form of a PACS
(Picture Archiving and Communication System).

Image data sets (the image data set IM and the reference image data set) may be three-dimensional data sets acquired, for instance, using a computed tomography system or a magnetic resonance imaging system. Here, the image information is encoded in a three-dimensional array of k times m times n voxels. Further, image data sets may relate to two-dimensional data sets, for instance acquired with an X-Ray facility, with the image information being encoded in m times n pixels. Further, the image data sets may comprise a time lapse of three- or two-dimensional medical images. When comparing follow-up medical examinations, data extracted from medical image data set is compared to data extracted from a reference medical image data set. Generally, image data set IM and the reference medical image data set show the same body part of a patient albeit at different points in time and, possibly, acquired using different imaging modalities. In general, the body part depicted will comprise various anatomies and organs. Considering the chest area, image data sets might, for instance, depict the lung lobes, the rib cage, the heart, lymph nodes, and so forth. While one of the image data sets (either the received image data set IM itself or the reference image data set) has been taken at an earlier examination at a first time, the respective other relates to a follow-up examination at a later stage at a second time. The second time may be hours, days, week, months, or years after the first time. Further, there may be intervening scans or procedures between the first time and the second time. In an embodiment, the medical image data sets have been acquired using the same or similar settings and parameters. Similar settings and parameters may include, for example, the same medical imaging modality 11, a similar dose (if available), the same phase timing, x-ray source voltage, contrast agent, MRI-protocol, and the like. Alternatively, the image data sets—despite of the fact that they depict the same body part—may have been acquired using different imaging modalities 11 and/or different settings for the imaging modalities 11.

As shown in FIG. 1, user interface 12 may comprise a display unit 12a and an input unit 12b. User interface 12 may be embodied by a mobile device such as a smartphone or tablet computer. Further, user interface 12 may be embodied as a workstation in the form of a desktop PC or laptop. The input unit 12b may be integrated in display unit 12a, e.g., in the form of a touch screen. As an alternative or in addition to that, the input unit may comprise a keyboard 12b, a mouse or a digital pen and any combination thereof. The display unit 12a is configured for displaying the image data set IM and/or the result of the image processing as performed by the central processing system 100/the processor 20.

Client 10 further comprises a client processing system 13 configured to execute at least one software component for serving the display unit 12a and the input unit 12b in order to provide a graphical user interface for allowing the user to select an image data set IM for upload to the central processing system 100 and/or to choose from the available reference data sets RDS within the graphical user interface. In addition, client processing system 13 may be configured to communicate with medical imaging system 11 and/or the central processing system 100, e.g., for uploading the image data set IM, receiving candidate reference data sets RDS for review by the user and/or receiving the result of the analysis provided by the central processing system 100. The user may activate the software component via user interface 12. He may acquire the software component, e.g., by downloading it from an internet application store. According to an example, the software component may also be a client-server computer program in the form of a web application running in a web browser. The client processing system 13 may be a general processor, central processing unit, control processor, graphics processing unit, digital signal processor, three-dimensional rendering processor, image processor, application specific integrated circuit, field programmable gate array, digital circuit, analog circuit, combinations thereof, or other now known device for processing image data.

Database 14 may generally be configured to store reference data sets RDS. The reference data sets RDS have been derived from corresponding image data sets IM by applying one or more image processing techniques. As such, the reference data sets RDS constitute a condensed or reduced set of information that enables a quantitative comparison between prior and/or follow-up examinations of a patient even without access to the underlying complete (raw) image data. Database 14 may be configured such that it can be queried by the central processing system 100 for the retrieval of reference data sets RDS. Of note, database 14 is optional to the distributed environment 1 in the sense that the role of database 14 may be taken over by central database 30 comprised in the central processing system 100. Further, database 14 may be embodied as part of an archive/review station comprised in the medical imaging system 11. Database 14 may be realized as a local or spread storage.

Specifically, reference data sets RDS may comprise two types of information. On the one hand they may comprise medical findings EMF, RMF extracted from the underlying image data sets. On the other hand, reference data sets RDS may comprise biometric data EBD, RBD. The medical findings EMF, RMF may in general relate to physiological observations extracted from image data by image processing which observations are relevant for arriving at a medical diagnosis. Examples for such information include the volume, cross-section, circumference, diameter and the like of a lesion, nodule, mass or other pathologically relevant features in the body part as extracted/measured from the respectively underlying examination. Moreover, it may comprise more high-level information such as degrees of malignancy, already known growth or shrinkage rates, values quantifying descriptive observables such as a state of the contour (e.g., either smooth or spiculated), a degree of calcification or fat deposition, or degree of solidity and so forth. What is more, the information may be in the form of cut-outs or clippings from the (reference) image data sets directed to pathological relevant areas (i.e., the medical findings EMF, RMF may comprise image data as well). In addition, the information may be semantic information describing the physiological information with words. The physiological information may be automatically extracted from medical image data sets using in principle known (computer-implemented) methods. However, it is also conceivable to use information that has been annotated by one or more users by hand, e.g., in the form of an already existing structured medical report.

In order to make medical finding EMF, RMF comparable across different image data sets, the medical findings EMF, RMF comprised in the individual image data sets need to be matched with one another. In other words, pairs of corresponding findings EMF, RMF, need to be identified. Further, it also should be established whether findings newly appeared or vanished. As already explained, doing so by straight-forwardly comparing of pixel and/or voxel values is generally not feasible as the coordinate systems of follow-up images data sets are usually not aligned very well. This is because imaging parameters such as the imaging window or the alignment of the patient may vary from examination to examination and further deviations may arise from inevitable anatomical changes and variations. Such anatomical changes may, for instance, relate to the breathing motion or to tissue deformations because of weight gain or loss. What is therefore needed are generalized reference or anchor points which can be used to calculate coordinate transformations between the respective coordinate systems using registration techniques (see below). These reference points should be easily extractable from the medical image data sets and sufficiently generic in the sense that they are applicable to a wide variety of image data sets possibly stemming from various imaging modalities. In this regard anatomic landmarks and surface meshes of anatomies and organs have proven very useful. Other options in this regard include segmentation masks or contours of anatomies and organs or even the medical findings EMF, RMF as introduced above themselves. The ensemble of suchlike data may be conceived as biometric fingerprint of a body part depicted in an image data set and is likewise comprised in the reference data set RDS as biometric data RBD. According to an embodiment, the reference data set RDS may be in the form of structured report in human readable format in which location-specific medical findings RMF are listed together with biometric data RBD.

The comparison of follow-up examinations using the reference data sets RDS is performed in central processing system 100 by processor 20. Processor 20 may comprise sub-units 21-24 configured to process the received image data set IM, retrieve corresponding reference data sets RDS pertaining to prior or subsequent examinations with respect to the received image data set IM and to quantify pathologically relevant changes between the data extracted from the image data set IM and the reference data set RDS. Processor 20 may be a general processor, a central processing unit, a control processor, a graphics processing unit, a digital signal processor, a three-dimensional rendering processor, an image processor, an application specific integrated circuit, a field programmable gate array, a digital circuit, an analog circuit, combinations thereof, or other now known device for processing image data. Processor 20 is a single device or may comprise multiple devices operating in serial, parallel, or separately. Processor 20 may comprise a real or virtual group of computers like a so called 'cluster' or 'cloud'. Such server system may be a central server, e.g., a cloud server, or a local server, e.g., located on a hospital or radiology site. Processor 20 may be a main processor of a computer, such as a laptop or desktop computer, or may be a processor for handling some tasks in a larger system, such as in the imaging system or the server. Processor 20 is configured by instructions, design, hardware, and/or software to perform the steps discussed herein. Further, processor 20 may comprise a memory such as a RAM for temporally storing the uploaded image data set IM and/or the reference data sets for further processing.

The central processing system 100 is configured to receive image data sets IM from one or more of the clients 10. To this end, central processing system 100 may comprise a suitable interface unit 40 for communicating with clients 10 over network 200.

Sub-unit 21 is a retrieval unit or module. It is configured to retrieve one or more reference data sets RDS which are associated (or can be associated) to the image data set IM received from a database 14, 30. The database in question may either relate to a database 13 at the respective client 10 or to database 30 of the central processing system. Sub-unit 21 may be configured to access and read the image data sets IM to extract a data identifier therefrom which can be used to query databases 14 or 30 for corresponding reference data sets RDS. This data identifier may for instance relate to a patient's ID or accession or file number. Further, sub-unit 21 may be configured to extract metadata from the image data set IM which may be used to narrow down the search. Such metadata may relate to the point in time the image data set IM has been acquired, the type of the image data set IM, the type of medical imaging modality 11 used for acquiring, the body part depicted in the image data set IM and so forth. This information may be retrieved from the header of the image data set IM and/or directly be extracted from the image data set IM by image processing. As an alternative or in addition to that, the metadata may be provided by the user upon uploading the image data set IM to central processing system 100. For instance, the metadata may be input via user interface 12 and forwarded to the central processing system 100 upon upload. Further, sub-unit 21 may be configured to apply one or more selection criteria when querying databases 14 or 30 for reference data sets RDS. The selection criteria may relate to the metadata introduced above. For instance, one selection criteria may involve specifically searching databases 14 or 30 for reference data sets RDS extracted from image data acquired with the same type of imaging modality 11 as the uploaded image data set IM.

Further, the search for reference data sets RDS may be constricted to data relating to the same body part as the uploaded image data set IM. To give another example, only such reference data sets RDS are retrieved that have been acquired within a set time window from the acquisition time of the image data set IM. Another selection criterion may relate to question whether reference data from prior or subsequent examinations is sought for. The selection criteria may be set by sub-unit 21 or interactively set by the user via user interface 12. Sub-unit 21 may further be configured to provide the retrieved data sets RDS to a user for review, approval and/or selection, e.g., by forwarding one or more candidate reference data sets RDS to user interface 12. If no reference data set RDS matches the selection criteria and/or no reference data set RDS can be found at all, sub-unit 21 may be configured to notify the user accordingly via user interface 12.

Sub-unit 22 is an image processing unit or module. Sub-unit 22 is configured to extract from the uploaded medical image data set IM information matching the information comprised in the reference data sets RDS so as to enable a comparison between the medical image data set IM and the one or more corresponding reference data sets RDS. Accordingly, sub-unit 22 is configured to extract from the image data set IM biometric data EBD corresponding to the reference biometric data RBD comprised in the reference data set RDS. Of note, "corresponding" does not require that there is a one-to-one correspondence between the extracted biometric data EBD and the reference biometric data RBD. Taking anatomic landmarks as example for biometric data, it is generally sufficient when at least some anatomic landmarks extracted from the medical image data set IM can be mapped to the anatomic landmarks comprised in the respective reference data set RDS to calculate a coordinate transformation function by registration unit 23. To ensure that the biometric data EBD, RBD sufficiently correspond, sub-unit 22 may be configured to analyze the reference biometric data RBD comprised in the reference data set RDS and process the image data set IM accordingly. Besides extracting appropriate biometric data EBD from the image data set IM, sub-unit 22 may be further configured to extract one or more medical findings EMF from image data set IM. Thereby, the medical findings EMF may relate to the same kind of information as mentioned above in connection with the reference biometric data RBD comprised in the reference data set RDS. For extracting the biometric data EBD and the physiological findings EMF from the image data sets IM, sub-unit 22 may be configured to implement the same or similar methods as used for extracting this information from the reference medical image data sets upon generating the reference data sets RDS.

Sub-unit 23 is a registration unit or module. Sub-unit 23 is configured to perform a registration of the extracted biometric data EBD and reference biometric data RBD. To this end, sub-unit 23 may be configured to determine which parts of the extracted biometric data EBD and the reference biometric data RBD correspond and perform the registration for the corresponding parts. Taking again anatomic landmarks and surface meshes as examples, sub-unit 23 may determine those anatomic landmarks and surface meshes which are comprised in both the extracted biometric data EBD and reference biometric data RBD and use these for the registration.

Once the corresponding parts of the biometric data and reference biometric data have been matched (e.g., by identifying corresponding pairs of data in the extracted biometric data EBD and the reference biometric data RBD), sub-unit 23 may calculate a coordinate transformation which essentially converts the biometric data EBD into reference biometric data RBD and vice versa, or, in other words, which minimizes the spatial distance between the corresponding parts of biometric data EBD and reference biometric data RBD. By construction, such transformation equals out any systematic (non-pathological) variations, deformations, and other differences in the metrics of the underlying image data sets. As these variations will generally be local and non-isotropic, the transformation functions will be as well. Accordingly, the calculation result provided by sub-unit 23 may be in the form of a two or three-dimensional transformation matrix or deformation field.

For performing the image registration, sub-unit 23 may apply one or more image registration techniques comprising rigid image registrations, affine image registrations, non-rigid image registrations and any combination thereof. To improve the result of the registration, sub-unit 23 may optionally be configured to mathematically fit the calculation result to one or more motion models for soft tissue deformation. Further, sub-unit 23 may be configured to divide or cluster the (reference) biometric data EBD, RBD into a plurality of segments or clusters, e.g., according to anatomies or organs comprised in the body part.

To this end, sub-unit 23 may be configured to run one or more segmentation filters, such as a lung segmentation filter, bone segmentation filter, liver segmentation filter and so forth. Alternatively, sub-unit 23 may simply cluster the biometric data EBD, RBD according to the semantic description of the individual data comprised in reference and extracted biometric data RBD, EBD. Sub-unit 23 may be further configured to generate individual deformation fields for each cluster using individual image registrations and motion models (which are possibly optimized for the organ or anatomy comprised in the respective segment or cluster).

Sub-unit 24 is a results generation and visualization module or unit. Sub-unit 24 is configured to compare the received image data set IM with the reference data set RDS using the results as provided by sub-unit 23. In particular, sub-unit 24 may be configured to apply the results of the registration so as to match corresponding medical findings EMF, RMF as extracted from the received image data set IM and comprised in the reference data set RDS. To this end, sub-unit 24 may be configured to map the extracted medical findings EMF onto the reference medical findings RMF (or vice versa). Another expression for "mapping" would be aligning (or co-aligning) the extracted medical findings EMF and the reference medical findings RMF. This may be done by sub-unit 24 by transforming the reference medical findings RMF into the coordinate system of the extracted medical findings EMF and vice versa by applying the transformation function output by sub-unit 23. Sub-unit 24 may further be configured to identify corresponding medical findings EMF, RMF on that basis. This may mean identifying pairs of corresponding medical finings in the extracted medical findings EMF and the reference medical findings RMF. This may further comprise identifying any medical findings which do have no counterpart in either the extracted medical findings EMF or the reference medical findings RMF as this indicates newly formed or vanished medical findings.

Sub-unit 24 may further be configured to identify and/or quantify a change in medical findings EMF, RMF based on the mapping/alignment and generate a result R on that basis. Moreover, sub-unit 24 may be further configured to translate or convert these results R into a suitable representation for displaying it to the user. The suitable representation can be in the form of an assistance image in which changes in medical findings are visually encoded. This may mean that changes are enhanced in the visualization. Sub-unit 24 may, for instance, be configured to run or execute an algorithm for rendering a semi-transparent overlay image from the quantified/identified change in medical findings to be superimposed over a correspondingly rendered image of the image data set IM. Moreover, sub-unit 24 may be configured to highlight changes in the form of symbols in the image data set IM.

The designation of the distinct sub-units 21-24 is to be construed by way of example and not as limitation. Accordingly, sub-units 21-24 may be integrated to form one single unit or can be embodied by computer code segments configured to execute the corresponding method steps running on a processor or the like of processing system 20. The same holds true with respect to client processing system 13. Each sub-unit 21-24 and client processing system 13 may be individually connected to other sub-units and or other components of the system 1 where data exchange is needed to perform the method steps.

For example, sub-unit 21 may be connected to database 30 for retrieving the reference data sets RDS and to client processing system 13 and/or user interface 12 for forwarding one or more candidate reference data sets RDS to a user for review. Processing system 20 and interface computing unit 13 together may constitute the computing unit as mentioned above. Of note, the physical layout of this computing unit, i.e., the physical distribution of interface computing unit 13 and sub-units 21-24 is, in principle, arbitrary. For instance, sub-unit 24 (or individual elements of it or specific algorithm sequences) may likewise be localized at the clients 10. The same holds true for the other sub-units 21-23. Specifically, processing system 20 may also be integrated in user interface 10.

Figure 2:
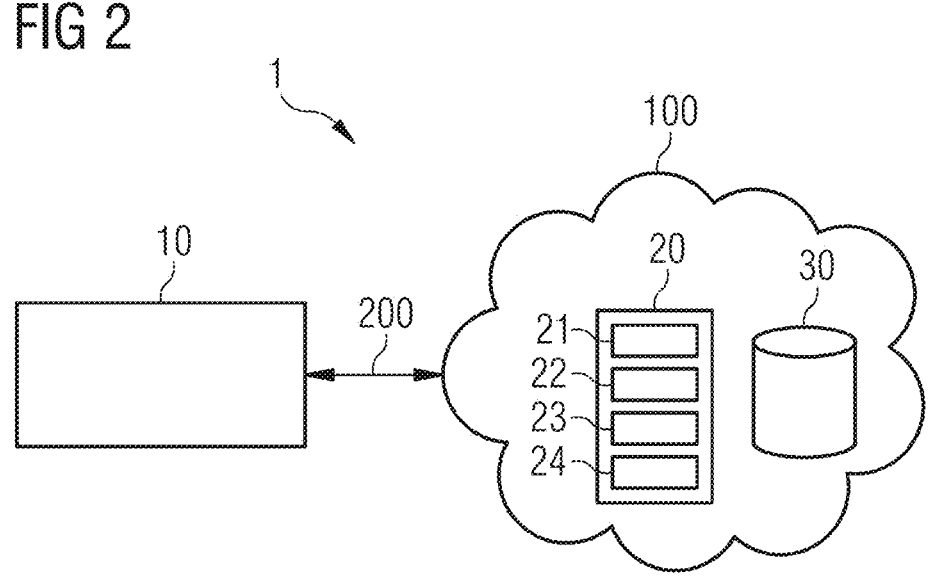
FIG. 2 depicts a distributed environment for comparing follow-up medical examinations according to an embodiment.

As already mentioned, processing system 20 may alternatively be embodied as a server system, e.g., a cloud server, or a local server, e.g., located on a hospital or radiology site. The implementation in the form of a cloud server is illustrated in FIG. 2 which depicts a distributed system 2 for follow-up reading according to an embodiment. Here, like reference numerals refer to like parts vis-à-vis FIG. 1. According to the implementation illustrated in FIG. 2, user interface 12 could be designated as "frontend" or "client" facing the user, while central processing system 100 could then be conceived as "backend". Communication between user interface 10 and processing system 20 may be carried out over network 200, e.g., using the https-protocol. The computational power of system 2 may be distributed between the central processing system 100 and the clients 10. In a "thin client" system, the majority of the computational capabilities exists at the central processing system 100. In a "thick client" system, more of the computational capabilities, and possibly data, exist on the clients 10.

Individual components of systems 1, 2 may be at least temporarily connected to each other for data transfer and/or exchange. Clients 10 communicates with central processing system 100 via an interface unit 40 to exchange, e.g., the image data sets IM, the reference data sets RDS and/or the processing results R. For example, central processing system 100 may be activated on a request-base, wherein the request is sent by client 10, e.g., by uploading an image data set IM to central processing system 100. Further, central processing system 100 may communicate with databases 14 or 30 or further data storage devices via interface unit 40. Specifically, the connection to the databases 14, 30 may involve an interface (as part of interface unit 40) compatible with the DICOM-standard (Digital Imaging and Communications in Medicine) and the retrieval of the reference data sets RDS may be carried out by a DICOM query and retrieve application class. Likewise, archiving further reference data sets may be carried out using the DICOM query and retrieve application class. Interface unit 40 for data exchange may be realized as hardware- or software-interface, e.g., a PCI-bus, USB or fire-wire. Interface unit 40 may be interfaced with network 200. Data transfer via interface unit 40 may be realized using a network connection. Network connection may also be wireless, e.g., as wireless LAN (WLAN or WiFi). Interfaces for data exchange together with the components for interfacing with the user may also be regarded as part of the aforementioned interface unit.

Figure 3:
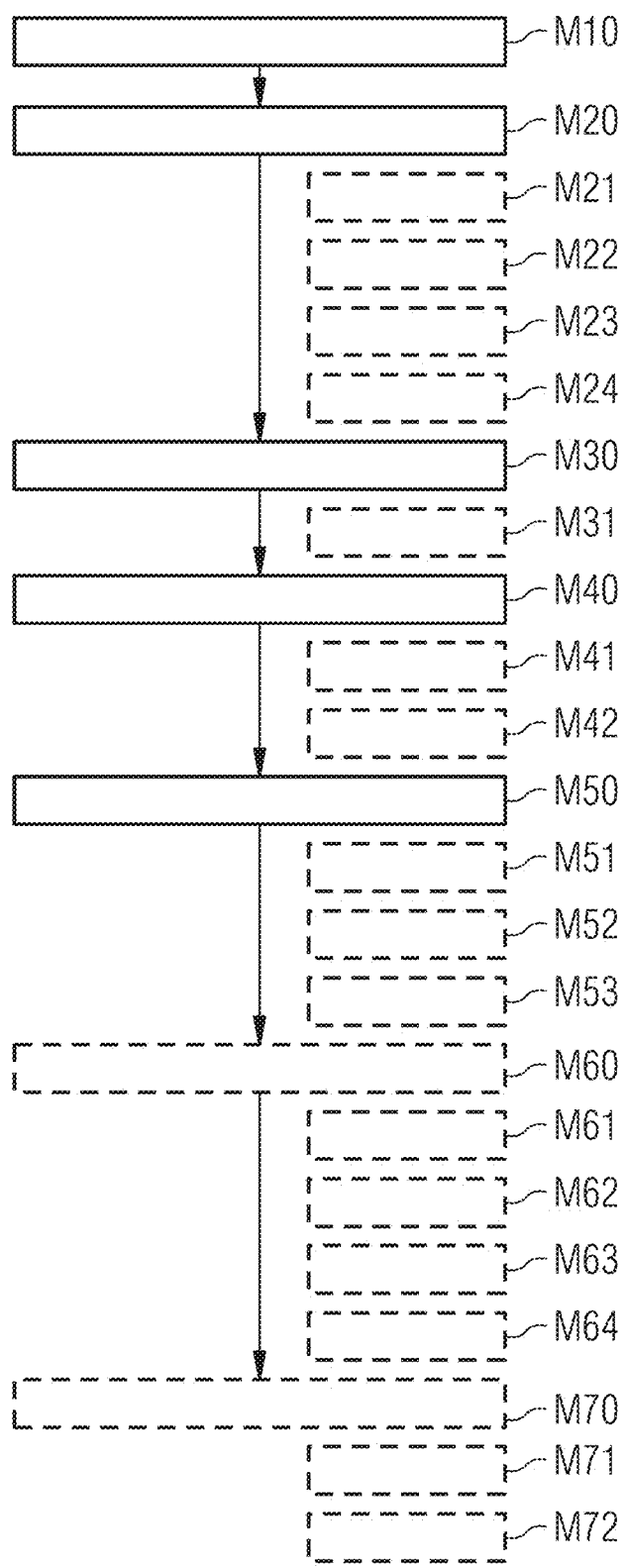
FIG. 3 depicts a block-diagram corresponding to a computer-implemented method for comparing follow-up medical examinations according to an embodiment, and FIG. 4 schematically shows the data streams between the system's components in conjunction with the main method steps according to an embodiment.
Figure 4:
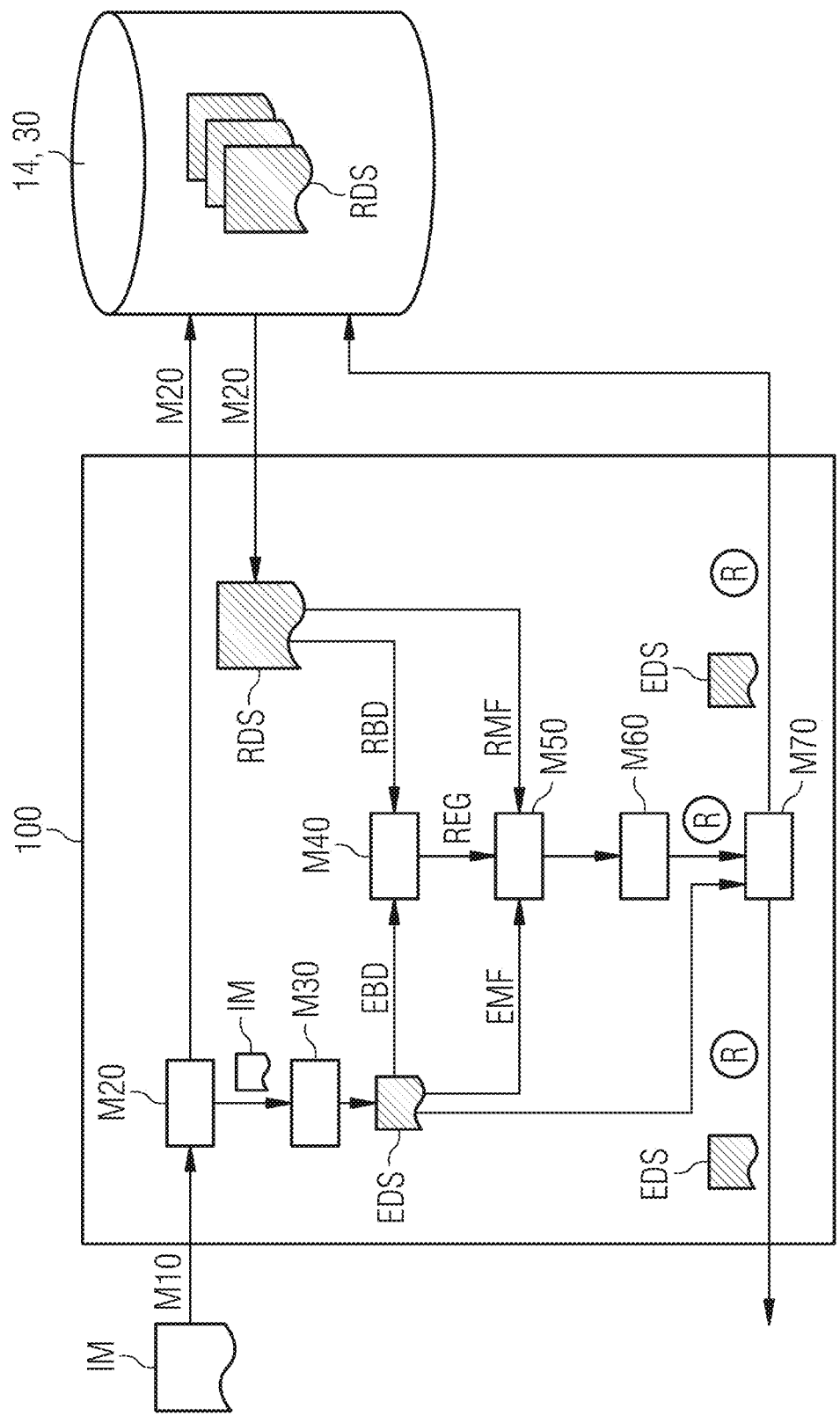

FIG. 3 depicts an inventive method for follow-up medical image data according to an embodiment of the present invention. Corresponding data streams are illustrated in FIG. 4. The method comprises several steps. The order of the steps does not necessarily correspond to the numbering of the steps but may also vary between different embodiments of the present invention. Optional steps or sub-steps are shown with dashed frames in FIG. 3.

In a first step M10, the image data set IM for which follow-up reading is requested is received. The image data set IM may be provided to the central processing system 100 by a user (which may be a radiologist, pathologist or other physician and healthcare personnel) by way of uploading the image data set IM to the central processing system 100.

A second step M20 is directed to retrieving at least one reference data sets RDS corresponding to the image data set IM from databases 14 and/or 30. To this end, the medical image data set IM may be read in optional sub-step M21 in order to extract information from the image data set IM based upon which the available databases 14, 30 can be queried for suitable reference data sets RDS. This information may include, data identifiers, e.g., in the form of an accession number or patient ID, information indicative of a patient, case and/or disease type, the type of medical image data set (2D, 3D, MR-data, CT-data, etc.), imaging modality and imaging parameters used, the point in time the image data set was acquired, treatments administrated to the patient, and so forth. This information may be read from the (DICOM)-header or the body of the image data set IM. As an alternative, all or part of this information may be supplemented by the user upon upload (which makes sub-step M21 optional).

In any case, the information thus gathered may be used to send a specific query to available databases 14 and/or 30. For instance, databases 14 and 30 may be queried for all reference data sets pertaining to the same patient as the image data set IM. In addition to that or as an alternative, one or more selection criteria may be defined in optional sub-step M22 with the help of which the search query may be further concretized. Such selection criteria may include: a desired time window between the acquisition of the image data set IM (at the first time) and the acquisition of the reference image data set underlying the reference data sets RDS (at the second time), whether prior and/or follow-up examinations are desired for comparison, whether results from different or like medical imaging modalities shall be considered, information if and how often a reference data set has already been used as a reference for follow-up reading, and so forth. Other than filtering the available reference data sets RDS, the selection criteria may further be used to calculate a relevance score and select reference data sets according to the relevance score in optional sub-step M23.

Figure 5:
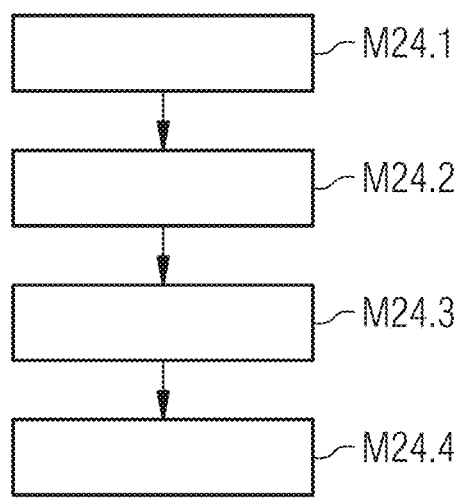
FIG. 5 illustrates the sequence of several optional sub-steps of the method according to FIG. 3.

For instance, the relevance score may be such that older reference data sets RDS score lower than more recent ones. The thus retrieved reference data set(s) may be forwarded to the clients 10 in optional sub-step M24 as "candidate reference data sets". As further detailed in FIG. 5, sub-step M24 may be divided into individual steps M24.1-M24.4 as follows: retrieving in M24.1, from the database 14 and/or 30 one or more candidate reference data sets, providing in M24.2 the one or more candidate reference data sets to a user for selecting, from the one or more candidate reference data sets, a user selected reference data set, receiving in M24.3 the user selection, and using in M24.4 the user-selected reference data set as the reference data set RDS. At the clients 10, the candidate reference data sets may be presented to the user in M24.2, e.g., via user interface 12 and preferably together with an indication of certain key information (time stamp, relevance score, etc.). The user may then select which one(s) of the reference data sets she or he wants to use for follow-up reading and further processing by the central processing system 100.

As for the database from which the reference data sets are retrieved in step M20, this may either be a local database 14 (sitting, e.g., at the site from which the medical image data set IM) has been submitted or database 30 of the central processing system 100 (c.f., FIG. 4). Selfspeaking, also both databases 14 and 30 or further (external) databases may be queried in step M20. Step M20 may be performed at least partially either on the side of the clients 10 or at the central processing system 100. Corresponding data exchange is included in this step where necessary. Preferably, step M20 is predominately performed in central processing system 100, with actions involving the clients being initiated by the central processing system 100.

Step M30 is an image processing step which is directed to extract, from the image data set IM, information for the ensuing registration and feature comparison with the reference data sets RDS. The ensemble of data thus extracted from the image data set IM is denoted as extracted data set EDS. The extracted data set EDS at least partly corresponds to the reference data set RDS. Step M30 may be performed in parallel or subsequent to step M20. In the latter case, characteristics of the retrieved reference data set(s) RDS may be read and the image data set IM can be processed based upon the read characteristics in optional sub-step M31. Thereby the characteristics may pertain to the kind of biometric data RBD and medical findings RMF comprised in the reference data set RDS. That way, when it is determined in sub-step M31 that the reference data set RDS comprises a given set of anatomic landmarks, the image data set IM may be deliberately processed to automatically extract anatomic landmarks optimally corresponding to the ones in the reference data set RDS. Especially if the biometric data relied on is highly standardized, sub-step M31 may also be omitted, however. Just like the reference data set RDS, the data extracted from the image data set IM in step M30 may comprise two types of information: one being the biometric information ("extracted biometric data" EBD) the other being medical findings ("extracted medical findings" EMF). As already explained, also the extracted biometric data EBD may comprise one or more medical findings EMF, however. Preferably, step M30 is performed in central processing system 100.

Once the image processing of step M30 is completed, the data EDS extracted from the image data set IM is principally in shape for comparing it to the reference data set RDS. To quantify changes from the reference data set RDS to the extracted data set EDS, the structured results respectively comprised have to be mapped. In other words, it is to be determined which one(s) of the medical findings RMF, EMF correspond to one another, which ones are new and which ones disappeared. If the locations of the medical finding RMF, EMF would be defined with respect to identical coordinate systems, this mapping would amount to a simple overlay. As already explained, the underlying coordinate systems are far from being identical, however.

By consequence, a transformation function needs to be calculated which is capable of transforming the respective reference data set RDS into the coordinate system of the extracted data set EDS and vice versa. This is done by way of performing a registration REG in step M40. In step M40, at least part of the respective reference data set RDS is registered with at least part of the extracted data set EDS. Essentially, this may comprise identifying corresponding data points in the respective reference data set RDS and the extracted data set EDS in optional sub-step M41.

Having identified such corresponding data points, it is possible to calculate the local offset between these corresponding points which provides an indication of the local shift in coordinate systems from the reference data set RDS to the extracted data set EDS. Doing this for a plurality of corresponding data points sufficiently distributed in the underlying image volumes already provides a good indication of the displacements and deformations between the respective reference data set RDS and the extracted data set EDS. To appropriately aggregate these individual contributions into a coherent two or three-dimensional transformation function or deformation field various registration techniques may be used. These techniques may comprise rigid registrations, affine registrations, non-rigid registrations, non-affine registrations and any combination thereof.

The registration tries to find a transform T which minimizes the spatial distances (according to an implementation: Euclidean norm for points and surface distance metrics for meshes) of the landmark locations for the two data sets. According to an implementation, this task can be formulated as follows: Assuming that N (generalized) landmarks have been found in both data sets and let $x_n$ and $\widehat{x_n}$ denote their spatial coordinates, and that the transform is determined by M parameters p1 . . . pM, the optimization task reads:

$$\min_{p_1,\ldots,p_M} \sum_n w_n dist_n(x_n, T(\widehat{x_n}, p_1, \ldots, p_M)),$$

where wn denote weighting parameters and distn the distance metric used (e.g. Euclidean distance, surface distance). In preferred embodiments, choices for T are translation (simple shift), rigid (shift and rotation), affine (rigid+ sheer) or deformable transformations.

Further, the registration may involve model fitting operations and segmentation, or clustering strategies as introduced above. The calculation of the transformation function may take place in a designated sub-step which is denoted M42. According to an embodiment, the registration is specifically based on registering the biometric data EBD, RBD respectively comprised in the reference data set RDS and the extracted data set EDS with one another. Preferably, step M40 is performed in central processing system 100.

In subsequent step M50, the registration REG is used to compare the extracted data set EDS with the reference data set RDS—and therewith the information extracted from the image data set IM with the information extracted from the underlying reference medical image data set. In order to automatically quantify pathological changes between the underlying examinations and assist the user in delivering a medical diagnosis, observations (findings, measurements, etc.) extracted from the follow-up image data sets have to be matched. This may involve transforming the locations of the medical findings EMF, RMF into a common coordinate system in sub-step M51 using the result of the registration REG. That way, the medical findings EMF, RMF are mapped to one another or, in other words, (co-)aligned with one another.

That followed, corresponding pairs of medical findings EMF, RMF can be identified and it may be determined if medical findings newly formed or vanished. In an example embodiment, for each pair of a finding from the reference medical findings RMF and a finding from the extracted medical findings EMF, a probability may be calculated that the two findings describe the same pathology, for example taking into account their spatial proximity after the mapping in step M51, whether they are of the same type and how similar other parameters are. In an example embodiment, pairs that most likely describe the same findings, are matched/linked until a certain threshold is reached. The remaining findings then most likely relate to new lesions that was not present earlier or an old lesion that was surgically removed, for instance.

Once the medical findings EMF, RMF have been matched, changes in medical findings may be quantified in optional sub-step M53. Quantifying changes may mean that measured parameters of the medical findings EMF, RMF are compared. For instance, the volume occupied by a lesion in the image data set IM can be compared to the volume of the same lesion as extracted from the reference medical image data set and the difference in volumes may be quantified. With that, an indication of the shrinkage or growth rates of the lesion can be provided. Preferably, step M50 is performed in central processing system 100.

In subsequent step M60, the quantified changes in medical findings are used to generate a result R. Result R may be in the form of a viewable result for a user, i.e., in a human readable format. As such, the result R may be in the form of a structured report in which the change in medical findings is indicated. For instance, the structured report may be in the form of a radiology report prefilled by the system with the outcome of the comparison of previous step M50. The report may be configured such that the user may complete the report, e.g., by dictating further observations and his/her impression. The generation of a structured report may take place in optional sub-step M61.

Further, the results R generated in step M60 may be in the form of a visualization. The visualization may be generated in optional sub-step M62. The visualization may comprise rendering one or more representations of the image data set IM with the changes highlighted for the user, e.g., by introducing symbols or numbers in the vicinity of the extracted medical findings EMF, applying color maps or heatmaps, and/or adjusting brightness or luminescence values of the rendering. The result of the rendering can be in the form of one or more assistance images indicating to the user where the changes occurred are and/or what magnitude they have. The rendering may be a two-dimensional rendering based upon an appropriate representation of the image data set IM such as a cross-section or slice through the image volume. The representation may be selected manually by the user, e.g., by scrolling through the image volume, or (semi-) automatically by the system.

Further, known volumetric rendering techniques such as ray-tracing or ray-casting or the like may be employed. In this regard, the user may specify parameters such as the viewing angle or the viewing distance. Preferably, this can be done in an interactive manner via user interface 12 with the help of a suited graphical user interface. The magnitude of the change may be visualized as a heatmap, e.g., as an overlay image on the image data set IM to help guide the image reading by the user. Here, a color gradient having a given color spectrum may be assigned to the magnitude of changes so that large positive changes (growth, newly occurring lesions etc.) are associated with one end of the color spectrum and large negative changes (shrinkage, disappearance) are associated to the other end of the color spectrum.

By providing or creating a representation or history of associated findings in the form of a table or a trending graph, yet another form of results R may be generated in optional sub-step M63. Of note, the results R may not only reflect the comparison of the image data set IM with one reference data set RDS but with a plurality of data sets. Accordingly, structured reports, assistance images and trending graphs may illustrate the change in medical findings over a plurality of follow-up examinations.

According to an embodiment the type of result R (e.g., structured report, assistance image, trending graph) may be interactively selected by the user via user interface 12. Yet another optional sub-step M64 is directed to forward the result(s) R to the user, e.g., via user interface 12. Step M60 may be performed at least partially either on user interface 12 or on central processing system 100. Corresponding data exchange is included in this step where necessary. Preferably, step M60 is predominately performed in central processing system 100, with actions involving the clients being initiated by the central processing system 100. In other words, step M60 is controlled by the central processing system 100.

Optional step M70 is a storing or archiving step. It may address both the results R generated (optional sub-step M71) as well as the data extracted from the image data set IM, i.e., the extracted biometric data EBD and the extracted medical findings EMF (optional sub-step M72). As shown in FIG. 4, archiving in both cases may take place in the local database 13 as well as in the system's database 40. Preferably, step M70 is implemented such that the user is given the opportunity to actively decide whether or not she or he wants the results R and/or the extracted data set EDS to be archived. This can be realized by a corresponding button in the graphical user interface running in user interface 12, for instance.

Upon importing, the extracted data set EDS may be formatted such as to correspond to the reference data sets RDS already stored in database 14 and/or 30. Further, data import may also include automated operations of tagging data as well as mapping the imported data to data already archived. The actions of tagging and mapping may be based on any metadata adhered to the image data set IM and/or any piece of supplementary information uploaded together with the medical image data set. For instance, the accession number, patient ID, image modality used and/or the time at which the examination was taken may be extracted from either the metadata or any other supplementary information and used to archive the extracted data set EDS in a systematic and readily retrievable manner within databases 14 and/or 30.

Prior to archiving, any data may be subjected to an appropriate filtering procedure in order to ensure that the archived data is anonymized. Step M70 may be performed at least partially either on user interface 12 or on central processing system 100. Corresponding data exchange is included in this step where necessary. Preferably, step M70 is predominately performed in central processing system 100, with actions involving the clients being initiated by the central processing system 100. In other words, step M70 is controlled by the central processing system 100.

Wherever meaningful, individual embodiments or their individual embodiments and features can be combined or exchanged with one another without limiting or widening the scope of the present invention. Advantages which are described with respect to one embodiment of the present invention are, wherever applicable, also advantageous to other embodiments.

The following points are also part of the disclosure:

1. Computer-implemented method for comparing follow-up medical examinations, the method comprising:
   receiving a medical image data set showing a body part of a patient at a first time;
   retrieving, from a database, at least one reference data set associated to the image data set, wherein the reference data set comprises reference biometric data having been extracted from a reference image data set depicting the body part of the patient at second time different than the first time, the reference biometric data defining locations of anatomies of the body part in the reference image data set;
   extracting, from the image data set, biometric data which define locations of anatomies of the body part in the image data set and which at least partly correspond to the reference biometric data;
   performing a registration of the reference data set with image data set on the basis the reference biometric data and the extracted biometric data;
   comparing the image data set with the reference data set based upon the registration.

2. Method according to 1,
   wherein the reference data set comprises one or more reference medical findings having been extracted from the reference image data set, the reference medical findings being respectively associated to locations in the reference image data set;
   wherein the step of extracting further comprises extracting, from the medical image data set, one or more medical findings associated to locations in the image data set;
   wherein the step of comparing comprises comparing the extracted medical findings with the reference medical findings, especially comprising quantifying a change in the medical findings.

3. Computer-implemented method for comparing follow-up medical image data, the method comprising:
   receiving a medical image data set showing a body part of a patient at a first time;
   retrieving, from a database, at least one reference data set associated to the image data set, wherein the reference data set comprises:
   reference biometric data extracted from a reference image data set depicting the body part of the patient at second time different than the first time; and
   one or more reference medical findings extracted from the reference image data set, the reference medical findings being associated to locations in the reference image data set;
   extracting, from the image data set, biometric data which at least partly correspond to the reference anatomic data and one or more medical findings associated to locations in the image data set;
   performing a registration of the reference data set with image data set using the reference biometric data and the extracted biometric data;
   comparing the extracted medical findings with the reference medical findings based upon the registration, especially comprising quantifying a change in the medical findings.

4. Method according to 2 or 3, further comprising the step of
   compiling a further reference data set based upon the extracted biometric data and the extracted medical findings; and
   forwarding the further reference data set to the database for storing it in the database.

5. Method according to any of points 2 to 4, wherein the step of comparing comprises matching extracted medical findings with reference medical findings using the registration.

6. Method according to any of points 2 to 5, wherein the step of comparing comprised aligning extracted medical findings with reference medical findings using the registration.

7. Method according to any of points 2 to 6, further with the steps of
   calculating a result based upon the quantified change; and
   forwarding the result to a user, and/or
   storing the result in a database;
   the result preferably being in the form of:
   a trending graph illustrating the quantified change in medical findings,
   a structured medical report comprising indications of the quantified change in medical findings, preferably in the form of one or more DICOM SR objects,
   a visualization viewable by a user visualizing the quantified change in medical findings, and/or
   any combination thereof.

8. Method according to any of points 2 to 7, further with the step of:
   generating a result viewable by a user based upon the quantified change, preferably by rendering an image of the medical image data set with the change highlighted.

9. Method according to any of the preceding points, wherein performing the registration comprises registering at least a part of the reference biometric data with at least a part of the extracted biometric data.

10. Method according to any of the preceding points, wherein performing the registration comprises respectively determining, in the reference biometric data and the extracted biometric data, mutually corresponding data and performing the registration based upon the mutually corresponding data.

11. Method according to any of the preceding points, wherein the reference data set is formatted according to the DICOM standard.

12. Method according to any of the preceding points, wherein the follow-up medical image data is received as upload by a user.

13. Method according to any of the preceding points, wherein the step of retrieving comprises:
    extracting a data identifier from the medical image data set; and querying the database for the reference data set using the data identifier.

14. Method according to any of the preceding points, further with the step of providing a database storing a plurality of reference data sets having been extracted from medical image data sets, wherein, in the step of retrieving, the at least one reference data set is retrieved from the database.

15. Method according to any of the preceding points, further with the step of retrieving, from the database, a second reference data set associated to the image data set, wherein the second reference data set comprises second reference biometric data having been extracted from a second reference image data set depicting the body part of the patient at third time different than the first time, the reference biometric data defining locations of anatomies of the body part in the second reference image data set;
    extracting, from the image data set, biometric data which define locations of anatomies of the body part in the image data set and which at least partly correspond to the second reference biometric data;
    performing a registration of the reference data set with image data set on the basis the reference biometric data and the second extracted biometric data;
    comparing the image data set with the second reference data set based upon the registration.

16. Method according to 15, further with:
    performing a second registration of the second reference data set with the reference data set on the basis the reference biometric data and the second extracted biometric data;
    comparing the reference data set with the second reference data set based upon the registration.

17. Computer-implemented method for comparing follow-up medical image data, the method comprising:
    receiving a medical image data set showing a body part of a patient at a first time;
    retrieving, from a database, a reference data set associated to the image data set, wherein:
        the reference data set has been extracted from a reference image data set depicting the body part of the patient at second time different than the first time, and
        the reference data set comprises a plurality of position-specific reference values respectively relating to locations in the reference image data set;
    extracting, from the image data set, an extracted data set comprising a plurality of position-related extracted values which respectively relate to locations in the body part of the image data set and which at least partly corresponds to the reference data set;
    performing a registration of the reference data set with the extracted data set by registering at least a part of the reference data set with at least a part of the extracted data set;
    comparing the reference data set with the extracted data set based upon the registration), in particular by quantifying a change from the reference data set to the extracted data set).

18. Method according to 17, wherein
    the reference values and the extracted values respectively comprise medical findings respectively associated to locations in the body part; and
    comparing comprises quantifying a change in the medical findings from the reference data set to the extracted data set.

19. Method according to 17 or 18, wherein
    the reference values and the extracted values respectively comprise a plurality of anatomic landmarks and/or surface meshes of anatomies; and
    the step of performing the registration is based on the anatomic landmarks and/or surface meshes.

20. Method according to any of points 17 to 19, further with the step of uploading the extracted data set to the database as further reference data set.

21. Computer-implemented method for comparing follow-up medical image data, the method comprising:
    receiving a medical image data set showing a body part of a patient at a first time;
    retrieving, from a database, a reference data set associated to the image data set;
    wherein the reference data set comprises:
        a set of reference anatomic landmarks extracted from a reference image data set depicting the body part of the patient at second time different than the first time, and
        one or more reference medical findings extracted from the reference image data set, the reference medical findings being associated to locations in the reference image data set;
    extracting, from the image data set, a set of anatomic landmarks which at least partly correspond to the reference anatomic landmarks and one or more medical findings associated to locations in the image data set;
    performing a registration of the reference data set with image data set by registering at least a part of the reference anatomic landmarks with at least a part of the extracted anatomic landmarks;
    comparing the extracted medical findings with the reference medical findings based upon the registration, in particular by quantifying a change in medical findings.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A computer-implemented method for comparing follow-up medical examinations, the computer-implemented method comprising:
   receiving a medical image data set showing a body part of a patient at a first time;
   retrieving, from a database, at least one reference data set associated to the image data set, wherein the at least one reference data set includes reference biometric data extracted from a reference image data set depicting the body part of the patient at a second time, different from the first time, the reference biometric data defining locations of one or more anatomies of the body part in the reference image data set;
   extracting, from the image data set, extracted biometric data defining locations of one or more anatomies of the body part in the image data set and at least partly corresponding to the reference biometric data;
   performing a registration of the at least one reference data set with the image data set based upon the reference biometric data and the extracted biometric data; and
   comparing the image data set with the at least one reference data set based upon the registration performed for a medical finding.

2. The computer-implemented method of claim 1,
   wherein the at least one reference data set includes one or more reference medical findings extracted from the reference image data set, the reference medical findings being respectively associated to locations in the reference image data set;
   wherein the extracting further comprises extracting, from the image data set, one or more medical findings associated to locations in the image data set; and
   wherein the comparing comprises comparing the one or more medical findings extracted with the reference medical findings, based upon the registration.

3. The computer-implemented method of claim 1, wherein the extracted biometric data and the reference biometric data respectively comprise at least one of:
   one or more anatomic landmarks, and
   one or more surface meshes of one or more anatomies comprised in the body part.

4. The computer-implemented method of claim 1, wherein the retrieving comprises:
   retrieving, from the database, one or more candidate reference data sets;
   providing the one or more candidate reference data sets to a user for selecting, from the one or more candidate reference data sets, at least one user selected reference data set,
   receiving the user selection; and
   using the at least one user-selected reference data set as the at least one reference data set.

5. The computer-implemented method of claim 1, wherein the retrieving comprises:
   providing one or more selection criteria; and
   retrieving the at least one reference data set by applying one or more of the selection criteria provided.

6. The computer-implemented method of claim 1, wherein the performing of the registration comprises calculating a transformation function mapping corresponding anatomic locations in the reference image data set and image data set to one another.

7. The computer-implemented method of claim 1, wherein the performing of the registration is based on at least one of a rigid registration, affine registration and non-rigid registration.

8. The computer-implemented method of claim 1, further comprising:
   compiling a further reference data set based upon the extracted biometric data; and
   forwarding the further reference data set to the database, the further reference data set being forwarded for storage in the database.

9. The computer-implemented method of claim 1, further comprising:
   calculating a result based upon the comparing; and at least one of forwarding the result to a user and storing the result in a database.

10. The computer-implemented method of claim 1, wherein
    the medical image data is received from a first site at a central processing system emote from the first site; and
    the retrieving, processing, performing and comparing are controlled by the central processing system.

11. A computer-implemented method for comparing follow-up medical examinations, the method comprising:
    receiving a medical image data set showing a body part of a patient at a first time;
    retrieving, from a database, a reference data set associated to the image data set, the reference data set having been extracted from a reference image data set depicting the body part of the patient at second time, different than the first time, and the reference data set including a plurality of position-specific reference values respectively relating to locations in the reference image data set;
    extracting, from the image data set, an extracted data set comprising a plurality of position-specific extracted values respectively relating to locations in the body part of the image data set, and at least partly corresponding to the reference data set;
    performing a registration of the reference data set with the extracted data set by registering at least a part of the reference data set with at least a part of the extracted data set; and
    comparing the reference data set with the extracted data set based upon the registration for a medical finding.

12. A system for comparing follow-up medical examinations, comprising:
    a computing unit, configured to:
    receive an image data set depicting a body part of a patient at a first time;
    retrieve, from a database, at least one reference data set associated to the image data set, the at least one reference data set including reference biometric data extracted from a reference image data set depicting the body part of the patient at a second time, different from the first time, and the reference biometric data defining locations of anatomies of the body part in the reference image data set;
    process the image data set, so as to extract, from the image data set, biometric data defining locations of one or more anatomies of the body part in the image data set and at least partly corresponding to the reference biometric data;
    perform a registration of the at least one reference data set with the image data set based upon the reference biometric data and the extracted biometric data; and compare the image data set with the at least one reference data set based upon the registration for a medical finding.

13. The system of claim 12, further comprising:
an interface configured to:
receive, from a site external to the system, medical image data sets; and
at least one of
communicate with the database storing a plurality of reference data sets having been extracted from medical image data sets; and
the database storing a plurality of reference data sets extracted from medical image data sets.

14. A non-transitory computer program product storing program elements which induce a computing unit of a system for comparing follow-up medical examinations to perform the method of claim 1 when the program elements are loaded into a memory of the computing unit.

15. A non-transitory computer-readable medium storing program elements, readable and executable by a computing unit of a system for comparing follow-up medical examinations, to perform the method of claim 1, when the program elements are executed by the computing unit.

16. The computer-implemented method of claim 2, wherein the comparing comprises comparing the one or more medical findings extracted with the reference medical findings, based upon the registration, by quantifying a change in the one or more medical findings.

17. The computer-implemented method of claim 2, wherein the extracted biometric data and the reference biometric data respectively comprise at least one of:
one or more anatomic landmarks, and
one or more surface meshes of one or more anatomies comprised in the body part.

18. The computer-implemented method of claim 2, wherein the retrieving comprises:
retrieving, from the database, one or more candidate reference data sets;
providing the one or more candidate reference data sets to a user for selecting, from the one or more candidate reference data sets, at least one user selected reference data set,
receiving the user selection; and
using the at least one user-selected reference data set as the at least one reference data set.

19. The computer-implemented method of claim 2, wherein the retrieving comprises:
providing one or more selection criteria; and
retrieving the at least one reference data set by applying one or more of the selection criteria provided.

20. The computer-implemented method of claim 5, wherein the selection criteria are based on at least one of:
an indication of an identity of a patient,
an indication of the depicted body part,
an imaging modality used for acquiring at least one of the image data set and the reference image data set,
a time window between the first and second times,
an indication whether the at least one reference data set relates to a prior or follow-up examination with respect to the image data set, and
an indication of prior selections of the reference data sets for comparison with a received image data set.

21. The computer-implemented method of claim 9, wherein the result includes at least one of:
a structured medical report,
a trending graph, and
a visualization viewable by a user.

22. The computer-implemented method of claim 11, wherein the comparing of the reference data set with the extracted data set based upon the registration, is achieved by quantifying a change from the reference data set to the extracted data set.

* * * * *